US006804929B2

(12) United States Patent
Kemnitz

(10) Patent No.: US 6,804,929 B2
(45) Date of Patent: Oct. 19, 2004

(54) ROTARY CAPPING APPARATUS AND FEEDBACK CONTROL SYSTEM FOR REGULATING APPLIED TORQUE

(76) Inventor: Tadeusz Kemnitz, 3701-P Highgate Dr., Durham, NC (US) 27713

( * ) Notice: Subject to any disclaimer, the term of this patent is extended or adjusted under 35 U.S.C. 154(b) by 0 days.

(21) Appl. No.: 09/879,623

(22) Filed: Jun. 13, 2001

(65) Prior Publication Data

US 2003/0041560 A1 Mar. 6, 2003

(51) Int. Cl.[7] .................................................. B67B 3/26
(52) U.S. Cl. ............................ 53/75; 53/317; 53/331.5; 53/361
(58) Field of Search ..................... 53/75, 317, 331.5, 53/361, 368, 490

(56) References Cited

U.S. PATENT DOCUMENTS

| | | | | |
|---|---|---|---|---|
| 2,202,181 A | * | 5/1940 | West ............................ | 53/360 |
| 2,297,720 A | * | 10/1942 | Schmutzer et al. ........... | 53/361 |
| 2,320,515 A | * | 6/1943 | Engle ........................... | 53/361 |
| 2,349,524 A | * | 5/1944 | sonnenberg ................. | 53/130.1 |
| 2,891,366 A | * | 6/1959 | Stover .......................... | 53/361 |
| 3,073,088 A | * | 1/1963 | White ........................... | 53/76 |
| 3,707,822 A | * | 1/1973 | van der Meer ............ | 53/331.5 |
| 4,312,168 A | * | 1/1982 | Desom .......................... | 53/49 |
| 4,535,583 A | * | 8/1985 | Tanaka et al. ................. | 53/75 |
| 4,765,119 A | * | 8/1988 | Aidlin et al. ................. | 53/308 |
| 5,301,488 A | * | 4/1994 | Ruhl et al. ..................... | 53/55 |
| 6,105,343 A | * | 8/2000 | Grove et al. .................. | 53/490 |
| 6,428,639 B1 | * | 8/2002 | Oldenburg et al. ........... | 156/64 |

* cited by examiner

Primary Examiner—John Sipos
Assistant Examiner—Louis Tran
(74) Attorney, Agent, or Firm—Clifford F. Rey

(57) ABSTRACT

A rotary capping apparatus and feedback control apparatus for regulating torque applied to screw-on type caps for containers is disclosed. The present system is integrated into a machine suitable for a clean-room environment. The apparatus includes a supporting frame whereon a computer-controlled driving mechanism including a servomotor for transmitting a predetermined torque to an inflatable gripping device actuated by compressed air for gripping and torquing such caps is provided. The inflatable gripper is imparted with automatic vertical height adjustment to accommodate containers of various sizes. The present rotary capping apparatus provides an integrated closed loop feedback control system utilizing a computer for setting parameters for regulating the application of such torque and a servocontroller interfaced for bidirectional communication with the computer. The servocontroller generates an output signal to the servomotor based upon the position of the rotary capping apparatus for precise torquing of the caps onto containers. The rotary capping apparatus also incorporates automated cap and container delivery mechanisms, which provide for synchronous advancement of the caps and containers to different stations within the machine for continuous processing.

13 Claims, 19 Drawing Sheets

ROTARY CAPPING APPARATUS AND FEEDBACK CONTROL SYSTEM FOR REGULATING APPLIED TORQUE

BACKGROUND OF THE INVENTION

1. Field of the Invention

The present invention relates to a rotary capping apparatus for applying a screw-on type cap to a filled container and, more particularly, to a rotary capping apparatus having an integrated feedback control system to precisely regulate the torque applied to such a container.

2. Description of Related Prior Art

Rotary capping devices are commonly used in industrial container filling operations such as pharmaceuticals wherein containers are filled with liquid or powder and then capped. In such filling operations empty containers are initially placed in so-called unscrambling devices, which are advanced to a filling line for filling, and then carried to the capping station via conveyor belts, starwheel devices and other apparatus for capping.

The screw-on type caps are disposed in unscrambling devices and then fed to the capping apparatus by way of conveyors and/or vibratory guides. Next, the caps are placed on the containers by a so-called pick-and-place mechanism. At the torquing station, the capping apparatus clamps the filled containers and grips the caps pre-positioned on the containers and rotates the caps onto the container. After a predetermined torque is applied by an adjustable chuck, the torquing operation is completed and the installed cap is released. The container clamping means is then released and the container is moved away from the capping apparatus by a suitable conveying means, for example, the belt or starwheel device that initially brought the container to the capping apparatus.

The containers capped by such a rotary capping apparatus must be subsequently unscrewed by hand to permit dispensing of the contents. Thus, the caps must be applied with sufficient torquing force so as not to leak during storage and transportation to the consumer, but may not be so tightly applied as to make it difficult for the consumer to remove the cap using only finger force. Consequently, the amount of torque applied must be within predetermined limits.

The prior art shows numerous patents in the field of capping devices for controlling the torque applied to such screw-on caps for containers. Most of the devices shown in the prior art use spring or air actuated friction slip clutches. In recent years, magnetic clutches or magnetic drives have also been frequently employed to control the torque applied to the caps.

Some examples of rotary capping devices in the prior art which utilize a disk clutch in the capping chuck are described in U.S. Pat. Nos. 4,558,554, 5,148,652 and 5,983, 596. These disk clutches are comprised of a number of friction plates stacked together. The amount of torque applied on the caps is controlled by a mechanical adjustment of the pressure in the friction plates. Once the desired torque is applied, the friction clutch will slip and interrupt the connection with the actuating means. At this point the gripping means are gradually opened to disengage from the cap and to allow the next container to be fed into the device, and the application head is lifted away from the container to allow the next container to be fed into the device. The disk clutches can also be actuated by pressure from a compressed air source. These clutches are known as air clutches and permit more accurate control of the pressure on the friction plates through an air pressure regulator and an air pressure gauge. In such air clutches an air piston is carried in the underside of an air clutch hub between a pair of piston seals and a retaining ring. The air clutch mechanism senses the applied torque between the cap and neck of a container and will allow the cap tightening discs thereon to stop once the desired torque is reached. The air pressure regulator can vary the air pressure to the air clutch piston to change the tension on the friction plate assembly thereby varying the torque setting.

Some examples of the use of magnetic clutches in the prior art are described in U.S. Pat. Nos. 5,197,258 and 5,437,139. In these patents, a pair of axially aligned circular cylinders is provided. Each of the cylinders is provided with cavities containing magnets. The maximum torque provided by the clutch is controlled by the vertical distance between the two disks through removable spacer disks of varying thickness. By providing a greater number of spacer disks, finer adjustment in torque values can be achieved.

The cap gripping mechanisms of the prior art are indeed diverse. Perhaps the most common mechanism is a tapered insert inside an aperture for engagement with caps of different sizes as exemplified in U.S. Pat. No. 5,148,652. Another common device is the use of two or three gripping jaws as disclosed in U.S. Pat. Nos. 4,232,499 and 5,983,596. The capping chucks in these patents have retaining jaws that are adapted to receive and support a cap and to cooperate with an internal torque release lever and torsion spring arrangement operative to release the jaws from the cap after a predetermined rotational torque is applied between the cap and a container.

Still another cap gripping mechanism is disclosed in U.S. Pat. No. 5,459,975. The chuck disclosed in this patent has a plate that provides a seat for a flat elastomeric ring, which constrains the ring against radial expansion. The elastomeric ring defines an opening to accommodate the cap to be tested. The housing further accommodates a so-called pusher member, which normally engages the elastomeric ring. A cam applies a force to move the pusher member against the elastomeric ring and this force coacts with the constraining force of the annular plate to cause the elastomeric ring to expand inwardly into tight gripping engagement with a cap disposed within the elastomeric ring permitting torque to be applied to the cap by rotation of the chuck without deforming the cap.

Although the methods and apparatus for capping containers described hereinabove are effective, the capping devices of the prior art have inherent limitations, which require further improvement. Due to the difficulty in making adjustments to the torque exerted during the cap-tightening process, the prior art mechanisms for tightening caps onto containers have resulted in leaking containers requiring time consuming and expensive reprocessing. Also the mechanisms for gripping such screw-on caps frequently damage the caps due to the use of excessive and/or non-uniform gripping forces. If too much compression force is applied to the cap, it may be damaged or deformed resulting in faulty application of torque, or the cap may bind and not screw onto the container properly causing the containers to be rejected.

The cap gripping mechanisms of the prior art need improvement for the following additional reasons. Such cap gripping mechanisms of the prior art often employ gripping jaws, which are mechanically complex, expensive, difficult to adjust for individual cap sizes and shapes or which are custom made for each different cap size and shape. Such mechanically complex gripping mechanisms also introduce potential operator error into the capping process requiring complicated adjustments and resultant time losses during production set-up for different products. In addition, such mechanical gripping jaws require manual set-up and do not provide for computer-controlled adjustment to different cap sizes. Additionally, prior art capping devices have generally been configured such that when chuck jaws have to be repaired or replaced, either due to changes in the sizes of the caps and/or containers being processed or due to damage to the jaws in use, extensive delays are encountered while the capping apparatus is disassembled to allow the chucking jaws to be serviced.

Prior art cap gripping mechanisms that utilize a tapered aperture for engagement with caps depend on frictional engagement between the aperture and the contact area of the cap. It is well known that friction is an unstable parameter and that the friction coefficient varies significantly with ambient conditions and the shape of contact surfaces often causing slippage. This slippage is more likely to occur when there is a relatively small contact area between the cap and tapered aperture of the gripping device. Such slippage will cause rapid wear of the gripping device having a detrimental effect on gripping performance as well. In addition, the fixed size of such tapered-aperture gripping mechanisms does not allow for computer-programmable changeover for different cap sizes.

Prior art gripping mechanisms utilizing an elastomeric ring that expands inwardly into tight gripping engagement with the cap have the inherent disadvantage of wearing relatively quickly because the elastomeric ring deforms all of its volume and still has a limited contact area with the cap. Also, different cap sizes and shapes require manual change over to different tooling. In addition, such cap gripping mechanisms do not allow for computer-programmable adjustment for different cap sizes.

Prior art torquing mechanisms having a disk clutch in the chucking device have the disadvantage of not utilizing any feedback in compensating significant errors affecting the capping torque. Large variations in such error is due to friction fluctuation in clutch disks due to changes in ambient conditions, especially temperature rising during the slippage, and wearing of slipping surfaces. Any required changeover to different torque settings will require numerous set-up samples and many adjustments and may still result in unstable torque. In addition, the disk clutch type torque mechanism does not allow for computer-adjustable torque over a large torque range.

Other prior art torquing mechanisms utilizing magnetic clutches in the capping chuck have the disadvantage of lacking any feedback in compensating for significant error affecting the capping torque. In such torquing mechanisms any changeover to different torque requires manual exchange of so-called spacer disks for varying the magnetic force. In addition, such magnetic clutch torquing mechanisms do not provide for computer-controlled adjustment of torquing changes over the entire torquing range.

SUMMARY OF THE INVENTION

Accordingly, the present invention is a rotary capping apparatus and feedback control system for regulating the torque applied to screw-on type caps for industrial containers such as pharmaceutical containers. The present capping apparatus and feedback control system is integrated into a machine suitable for so-called clean room production, which provides for automated, sterile processing of such caps and containers. In the present invention such caps are gripped by an inflatable chucking device actuated by compressed air including an elastomeric insert that grasps the entire surface of the cap and not just a few contact points about a top edge of the cap as in prior art devices. Thus, in the present apparatus the pressure applied via the inflatable chucking device can be minimal. This significantly increases the life of the tooling and the stability of performance, reduces pressure on the periphery of the cap, and also prevents deformation of the cap.

The present capping apparatus also provides for positive gripping, that is, undesired slippage or slippage as a means of metering the torque is totally eliminated. The gripping force is sufficient to prevent any slippage between the cap and the inflatable chucking device. The minimum required gripping force can be varied for different caps and can be adjusted by a computer-programmable pressure regulator thereby providing programmable changeover for different applications. This eliminates operator involvement and associated human error and reduces production down time by allowing immediate changeover by selection of new parameters from a computer console. The gripping force is released by purging (or vacuuming for increased speed) the pressurized air from the inflatable elastomeric insert surrounding the cap.

The present invention is also able to control torque more accurately by the use of a closed loop feedback control system including a servomechanism to control the applied torque. In the present feedback system a comparison between the actual process condition and the desired condition is made. The difference between these two signals (i.e. the error) is fed into the control system, which uses this information to alter the output signal to attain the required torque value calculated as: Error signal=set point−measured value. More specifically, in this application the actual torque being applied on the caps can be continuously fed back into the system for further action until the desired torque applied on the caps is reached. The present apparatus uses a proportional, integral and derivative known as a (PID) control system to control the applied torque for purposes of this invention. Such a PID control system consists of the following major components: a central processing unit (CPU), an input section, and output section, a power supply and a computer program.

The torque in the present capping apparatus is applied to the cap via a computer (CPU) controlled servomechanism. The servomechanism is engaged with the inflatable chucking device and executes closed loop PID control with position feedback, which results in precise torque application. Moreover, the value of the applied torque is adjustable from the computer console allowing for immediate changeover to different products, and eliminates any operator error associated with mechanical adjustments. The driver of the servomechanism is a servomotor. When the desired torque value is reached, the CPU immediately interrupts the PID controlling loop and removes voltage from the servomotor.

This system represents a significant improvement over the prior art capping devices described hereinabove wherein so-called open-loop control is used. In such devices no information is fed back to the system to determine whether the desired output was achieved and consequently a large error in the desired applied torque may result. Many outside influences affect the operation of such prior art capping devices. For example, the friction coefficient varies significantly with ambient conditions and shape of the cap engaging surfaces often causing slippage. Such slippage is more likely to occur due to a relatively small contact area between the cap and tapered aperture of the gripping chuck. Such slippage will often cause rapid wear of the gripping chuck and will generate heat. Both the resultant wear of the gripping chuck and the heat generated adversely impact the accuracy of the applied torque.

The present rotary capping apparatus also features automatic secondary height adjustment functions such that the machine will automatically set the vertical height of the cap dispensing mechanism based on a computer program for a specific product selected. This function is carried out manually in the prior art devices.

Other features and technical advantages of the present invention will become apparent from a study of the following description and the accompanying drawings.

BRIEF DESCRIPTION OF THE DRAWINGS

The novel features of the present invention are set forth in the appended claims. The invention itself, however, as well as other features and advantages thereof will be best understood by reference to the following detailed description of an illustrative embodiment when read in conjunction with the accompanying figures, wherein:

FIG. 7B' is also a cross-sectional view taken through the capping head along line B—B of FIG. 6 showing the inflatable chuck in an inflated condition;

DETAILED DESCRIPTION OF THE PREFERRED EMBODIMENTS

Figure 1:
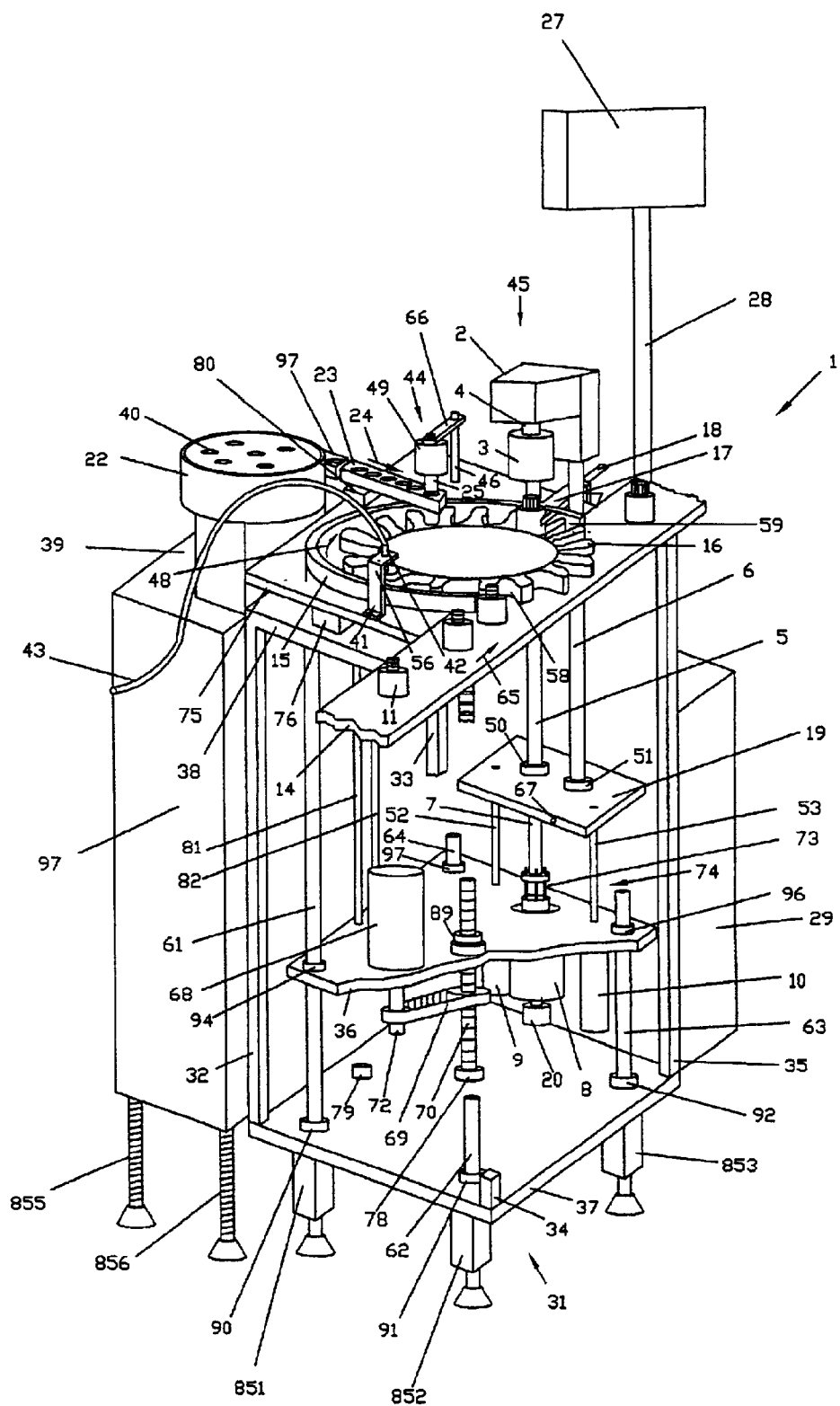
FIG. 1 is a cutaway perspective view of a rotary capping apparatus in accordance with the present invention.

With further reference to the drawings there is shown therein a rotary capping apparatus in accordance with the present invention, indicated generally at 10 and illustrated in FIG. 1. The rotary capping apparatus 10 includes a cap placement station, indicated generally at 44, a cap torquing station, indicated generally at 45, and an optional filling station, indicated generally at 41. The present capping apparatus 10 may further include a transparent safety shield (not shown) affixed thereto so as to extend downwardly over the cap driver assembly 401 to protect the operator of the device. It will be appreciated by those skilled in the art that the cap placement station 44, cap feeder bowl 22, and optional filling station 41 are all of conventional design.

The capping apparatus 10 further comprises a frame structure shown generally at 31, comprising a plurality of vertical frame members 32,33,34,35. The frame structure includes two horizontal plates, namely a bottom plate 37 and a top plate 38 that are fixedly attached to the vertical frame members 32–35, which extend therebetween. It will be noted that members 33 and 34 are partially cutaway in FIG. 1 to show the interior of the present apparatus. Four adjustable legs 851, 852, 853, and 854 (not shown) are attached to the bottom plate 37 to support the structure and provide for height adjustment, which is accomplished by turning the corresponding foot of each respective leg 851–854 in a known manner. The present capping apparatus 10 also includes sheet metal side covers (not shown) which enclose the frame structure.

A vibratory feeder bowl or unscrambling device 22 is fixedly secured to a feeder bowl base 39, which is enclosed by a sheet metal cover 97. The feeder bowl base 39 is separately supported by legs 855, 856, 857 (not shown), and 858 (not shown). The feeder bowl 22 functions to receive and dispense caps 40 therefrom for installation on containers 11. The feeder bowl 22 orients the caps 40 and discharges them in series with their threaded ends down into a transfer track 23. Caps 40 are transported from the bowl 22 onto the transfer track 23 via the feeder track 99. A small gap exists between the feeder track 99 and the transfer track 23 such that vibrations from the feeder bowl 22 are not transmitted to the transfer track 23.

Figure 14:
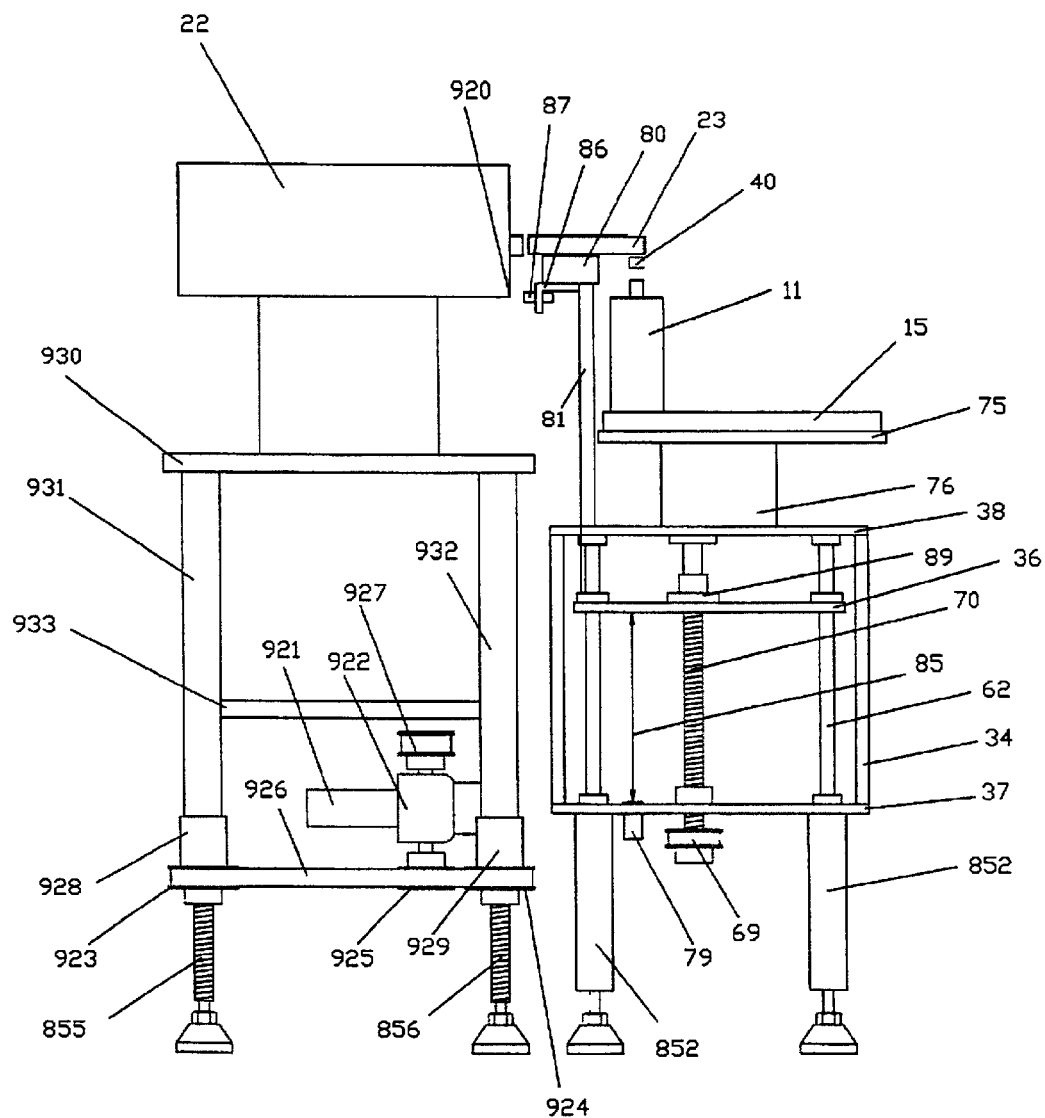
FIG. 14 is an orthogonal view the present rotary capping apparatus showing the components thereof which effectuate vertical height adjustment with various other components deleted for clarification purposes.

The transfer track 23 is mounted on track support plate 80, which in turn is supported by shafts 81 and 82 as more clearly shown in FIG. 14. Once a product is selected for processing, the present system will automatically move the transfer track 23 to the correct vertical height required to process the product selection. Shafts 81 and 82 are attached to carrier plate 36 and provide for automatic adjustment of the height of the transfer track 23 as described hereinafter in further detail.

It will be appreciated that transfer track 23 has an inlet portion aligned with the outlet portion 22a of the feeder bowl 22. The caps 40 are discharged into track 23 with their threaded ends face down. A track cover (not shown) is mounted on the track 23 to keep the caps from stacking on top of one another. The caps 40 move along the track 23 in the direction indicated by the directional arrow 24 in FIG. 1. The end of the track 23 is disposed adjacent to the cap placement station 44.

The cap placement station 44 is reciprocated up and down by a shaft 46, which is positioned within a bearing (not shown) located in the top plate 38. The shaft 46 is driven pneumatically by an air cylinder mounted on carrier plate 36. A drive motor 49 is mechanically coupled to shaft 46 by a bracket 66. A plunger 25 is connected to drive motor 49 and rotated in timed relationship to the capping apparatus cycle. A conventional belt and pulley system (not shown) is used to vary the speed of the motor 49.

The outlet end of the transfer track 23 is provided with a cap retaining means (not shown), which prevents the leading cap 40 from falling off the track 23. For example, the cap retaining means can be a spring-biased pair of levers or a rubber gasket with cutouts that will open up when downward force is applied to a cap 40. Adjacent to the cap retaining means there is also provided an optical sensor (not shown) to detect the presence of a cap 40 ready for cap placement and to send a signal to a computer integrated with the present apparatus. The caps 40 slide with their open, threaded ends down by gravity or under the urging of vibratory pulses or other suitable means. Typically the container caps 40 applied by the capping apparatus 10 have an internal right-handed thread formed therein and adapted for threaded cooperation with a mating external thread formed on the upper neck of the containers 11. In operation, plunger 25 pushes the leading cap 40 onto the containers 11. The caps 40 are loosely applied at this stage and may be partially threaded onto the necks of the containers 11.

The optional filling station 41 includes a fluid discharge nozzle 42, tubing 43, and bracket 56 to hold the discharge nozzle 42. The remainder of the filling mechanism is of conventional design and is not shown. The tubing 43 carries the fluid from a pumping means (not shown) in the filling mechanism to the discharge nozzle 42, which is mounted on bracket 56 as shown.

The present rotary capping apparatus 10 includes a drive mechanism and associated electronic circuitry and controls that drive and rotate a starwheel 16 that indexes the containers 11 one step at a time as they are filled, capped and torqued. The containers 11 are supported by a bottle support plate 75, which is fixedly mounted on a plurality of blocks 76 on the plate 38. Appropriate optical sensors (not shown) are positioned in the capping apparatus 10 to indicate the presence of containers 11 at the start of each cycle.

In operation, a plurality of containers 11 having external threads adjacent the top opening thereof are sequentially transported via conveyor system 14 for pick-up at the entry slot 58 of the starwheel 16. Once all the stations of the capping apparatus 10 have a container 11 in position, the production operation can start. During the production operation of the capping apparatus 10, the filling, capping and torquing stations all operate simultaneously. Once all the stations have completed their function, the starwheel 16 is indexed and the containers 11 advance one position. A new container will enter the entry slot 58 and a torqued container will exit from the exit slot 59. The conveyor system 14 is driven in the direction indicated by directional arrow 65 using known driving means (not shown). Optical sensors (not shown) are used to sense the location of the containers 11. These optical sensors transmit signals via electrical circuits (not shown) that interrupt the operation of the capping apparatus 10 in the event of a malfunction of the equipment. The actuation and deactuation of the various pneumatic cylinders and electrical motors utilized in the present device are controlled by a central processing unit (CPU) that is installed in the control cabinet 29.

At the filling station 42 the containers 11 are filled; at the cap placement station 44 a cap is placed and partially threaded onto the neck of a container 11; and at the torquing station the cap 40 is fully threaded to a predetermined torque. When the filled and partially capped containers 11 arrive at the torquing station 45, a clamping block 17 holds the containers 11 in position. The clamping block 17 is operated by a pneumatic cylinder 18, which is actuated via an electrovalve (not shown). The pneumatic line and associated electronics to extend and retract the clamping cylinder 18 are omitted for purposes of clarity in FIG. 1.

During the torquing operation the loosely capped containers 11 are held securely at the torquing station against the starwheel 16. A clamping block 17 mechanically coupled to a pneumatic cylinder 18 is free to move forward and backward to clamp and release the containers 11. The pneumatic line and associated electronics to extend and retract the clamping cylinder 18 are also omitted for clarity. The clamping block 17 is shown in its extended position in FIG. 1. Clamping the containers 11 in this position prevents them from rotating when caps 40 are being torqued on to seal the containers. The clamping force with which the containers 11 are secured is adjustable by a compressed air regulator and gauge (not shown) so as to apply only sufficient force to hold the containers 11 against rotation under the applied torque and not so high as to damage the containers.

Once a container 11 at the torquing station 45 has been torqued to the desired setting, the clamping block 17 will retract to permit the starwheel 16 to index the next set of containers 11. The starwheel 16 rotates in a clockwise direction as viewed from the top as shown by directional arrow 48. A semicircular starwheel guide 15 is disposed to the outside of the starwheel 16. The starwheel guide 15 and the starwheel 16 are configured and dimensioned such that there is a loose fit of the containers 11 and there is minimal friction between the containers 11 and the guide 15 during operation. The starwheel guide 15 does not extend 360° as it has a section removed to allow incoming containers 11 to enter and outgoing containers 11 to exit. Guide rails (not shown) serve to guide the containers 11 into and out of the starwheel 16. With each closing of the clamping block 17, a new container torquing cycle is initiated by the present capping apparatus 10 as described hereinafter in further detail.

Referring now to the torquing station 45, its operation will now be considered in detail. Prior to starting the torquing operation, the capping head 12 is moved to its optimal vertical position by the movement of horizontal carriage plate 36. Such optimal vertical position is determined by the height of the container 11 to be torqued. The horizontal carriage plate 36 serves as a base for all the mechanisms that must be adjusted for variations in container height. In particular, the servomechanism which drives the cap driver assembly 401 is attached to the horizontal carriage plate 36.

The vertical height adjustment motor 68 is mounted on horizontal plate 36. Motor 68 controls the height of the capping head 12 by the rotation of shaft 72, which is transmitted to lead screw 70 by way of belt and pulley system 69. The lead screw 70 is mounted on plate 37 by bearing 78 such that it is free to turn, but may not move in the vertical direction. A lead nut 89 is attached to the carrier plate 36 and engages the lead screw 70. When the lead screw 70 is turned the lead nut 89 causes carriage plate 36 to move up and down, which in turn moves the capping head 12 vertically. Vertical shafts 61, 62, 63 and 64 extend between and are coupled to bottom plate 37 and top plate 38 by a collar on each end of the respective shafts. Collars 90, 91, and 92 are shown in FIG. 1. Four linear bearings (only three of which are shown namely 94, 96, and 97) are disposed on plate 36 to engage and move plate 36 up and down the vertical shafts 61–64.

Leadscrew 70 is supported by bottom bearing 78 and top bearing 77 as most clearly shown in FIG. 14. An ultrasonic transmitter 79 capable of measuring the distance to the carriage plate 36 is disposed on support plate 37 as also seen in FIG. 14.

Referring again to FIG. 1, the capping head 12 is supported by vertical hollow shafts 5 and 6. Each of the vertical hollow shafts 5 and 6 can move vertically inside linear bearing blocks (not shown) that are fixedly attached to horizontal plate 38. The outer portion of the shafts 5 and 6 serve as bearing races sliding up and down in the bearing blocks. On the bottom portion, the vertically parallel, hollow shafts 5 and 6 are attached to the vertical motion driver plate 19 by collars 50 and 51, which are fixedly attached to driver plate 19. On the top portion, hollow shafts 5 and 6 are mechanically connected to the capping head 12.

Vertical motion driver plate 19 moves up and down by the action of a linear actuator, indicated generally at 74, and being comprised of pneumatic cylinders 9 and 10. Cylinders 9 and 10 are fixedly attached to horizontal carriage plate 36. Plate 36 contains clearance holes (not shown) for accommodating the extension rods of cylinders 9 and 10, which are shown respectively at 52 and 53. When the piston rods of cylinder 9 and 10 are retracted the capping head 12 is in its lower position Such lower position is used for torquing the containers 11. The upper position is used when the containers 11 are moved underneath the cap driver assembly 401. Thus, the vertical motion driver plate 19 is imparted with vertical movement by the action of pistons 9 and 10.

Compressed air for inflating the elastic gripper 201 is supplied from a compressor means (not shown) via an air/vacuum port 67. The port 67 is connected to hollow shaft 6 by a channel or orifice inside plate 19. A regulating valve and pressure gauge (not shown) are utilized by the operator to manually adjust the air pressure in the elastic gripper 201 disposed within the cap driver assembly 401 as most clearly seen in FIG. 4. This provides control of the gripping force applied to a cap 40 during the torquing operation. At the same port 67 shown in FIG. 1, a vacuum source is also connected to permit quick deflation of the insert 201 at the end of each torquing cycle.

In general, the inflatable insert 201 wraps around the entire periphery of a cylindrical cap. However, the insert 201 is also capable of gripping caps of an irregular shape such as caps (not shown) having a pour spout because the insert 201 is sufficiently flexible to conform to an irregular shape. Advantageously, this permits a reduction of the pressure applied to such a cap and avoids damage thereto.

Still referring to FIG. 1, a servomotor 8 is mounted on horizontal carriage plate 36. Servomotor 8 is electrically connected to a servoamplifier. Further description of how the servomotor 8 is driven by the servoamplifier is provided in conjunction with FIG. 8. At the upper end thereof servomotor 8 includes a spline mechanism, indicated generally at 73, that drives a rotatable drive shaft 7. The operation of the spline mechanism 73 will be described in further detail in connection with FIG. 7.

On the lower end thereof servomotor 8 includes an encoder 20. Encoder 20 is electrically connected to a servocontroller (not shown). Drive shaft 7 extends into the capping head 12 within the hollow shaft 5. This permits rotational motion of shaft 7 inside the hollow shaft 5 even while shaft 7 is moving up and down. The rotational motion of shaft 7 is transmitted to spindle shaft 4 by a gear mechanism shown and described in connection with FIG. 6.

Figure 2:
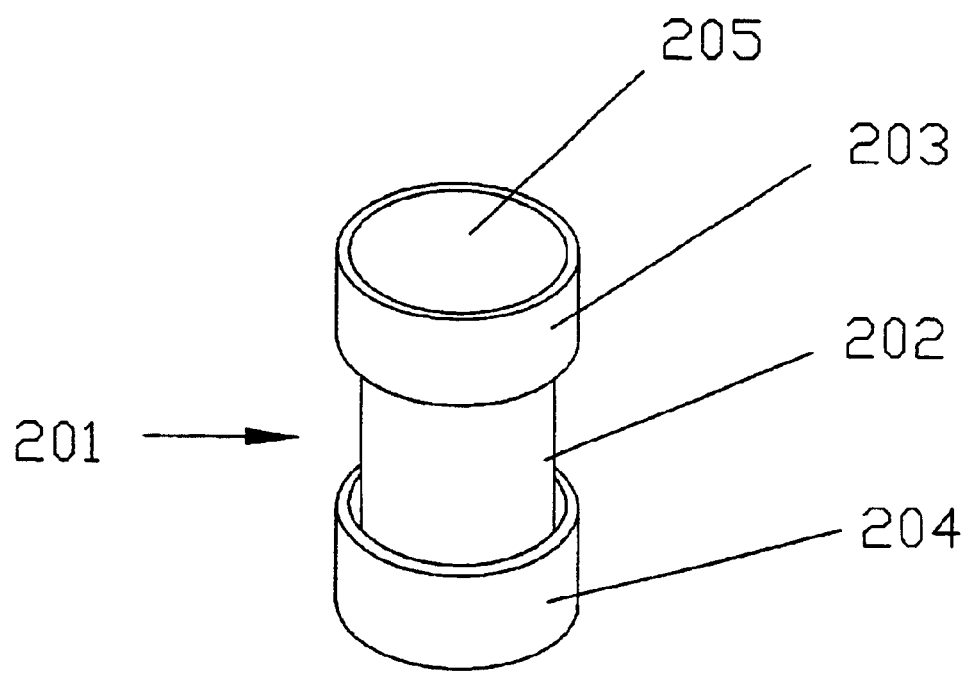
FIG. 2 is a perspective view of the inflatable chuck insert of the present invention.
Figure 4:
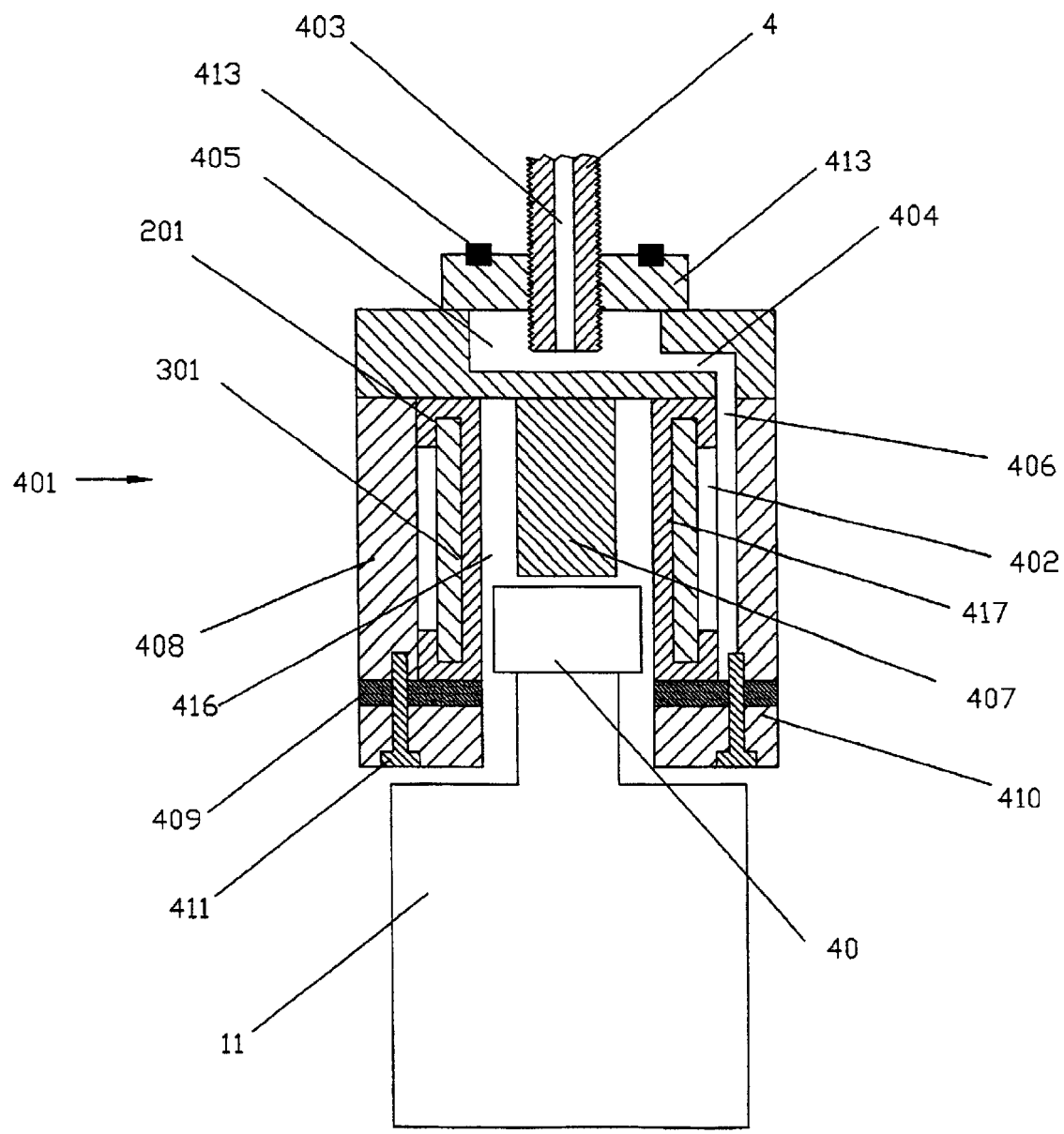
FIG. 4 is a cross-sectional view taken through the cap driver assembly of the present invention showing the components thereof.

FIG. 4 depicts a cross-sectional view of the cap driver assembly 401 in its operative position in relation to a container 11 disposed underneath it. In this view the container 11 has been loosely capped at the cap placement station 44. The cap driver assembly 401 encloses the elastic gripper 201, which is disposed in functional position around the cylindrical sleeve 301 as shown in FIG. 4. The elastic insert 201 comprises a cylindrical body 202 and two integrally formed, overhanging flanges 203 and 204 as most clearly shown in FIG. 2. A circular cavity 205 extends along the entire length of the insert 201. In the preferred embodiment the inflatable insert 201 is a unitary construction being fabricated of any elastomeric material of suitable physical and chemical properties for this application.

The inflatable insert 201 is dimensioned such that when the insert 201 is in a deflated condition, it will provide a loose fit with a cap 40 within the cap driver assembly 401 in position over the cap 40 as shown in FIG. 4. Prior to the torquing operation the inner surface of the elastic insert 201 surrounds the entire circular periphery of the cap 40 as illustrated.

The cap driver assembly 401 further comprises a housing 408 having a central cavity 416. A cap stabilizing plunger 407 is disposed in cavity 416 of the cap driver assembly 401 to ensure that any misaligned caps can be straightened prior to starting the torquing operation. The cap stabilizing plunger 407 can be either rigid or resilient in construction.

The top portion of the cap driver assembly 401 has affixed to it a circular plate 413 that is threaded to receive the spindle shaft 4. The top portion of plate 413 contains a groove for seating an O-ring 415. When the assembly 401 is threaded onto the spindle shaft 4, the O-ring 415 is compressed and forms an air tight connection between the capping head 12 and the cap driver assembly 401. Of course, the cap driver assembly 401 can be easily removed by unscrewing it from the spindle shaft 4. Thus, the insert 201 is replaceable without requiring major disassembly of the rotary capping apparatus 10 during maintenance procedures.

Referring now to FIG. 4 in conjunction with FIG. 1, the sequence of operations for a capping cycle will now be described. The starwheel 16 first advances a filled and loosely capped container 11 to the torquing station 45. Movement of the containers 11 and the capping head 12 is synchronized such that each container 11 is positioned vertically and axially underneath the cap driver assembly 401. Clamping block 17 clamps the container 11 underneath the cap driver assembly 401 in preparation for torquing. The capping head 12 then descends to its lowermost position, which is slightly above the upper end of the container 11. The capping head 12 moves down a predetermined distance, which has been determined by the initial height of the cap driver assembly 401 and the height of the container 11.

Thereafter, the elastic gripper 201 inflates into tight gripping engagement with a cap 40 disposed within the insert 201 such that torque can be applied to the cap 40 by rotation of the cap driver assembly 401 without deforming or damaging the cap 40. It will be appreciated by those skilled in the art that the elastic insert 201 can expand only in a direction toward the longitudinal axis A of the cap driver assembly 401 due to the constraining effect of the surface of the sleeve 301.

Figure 3:
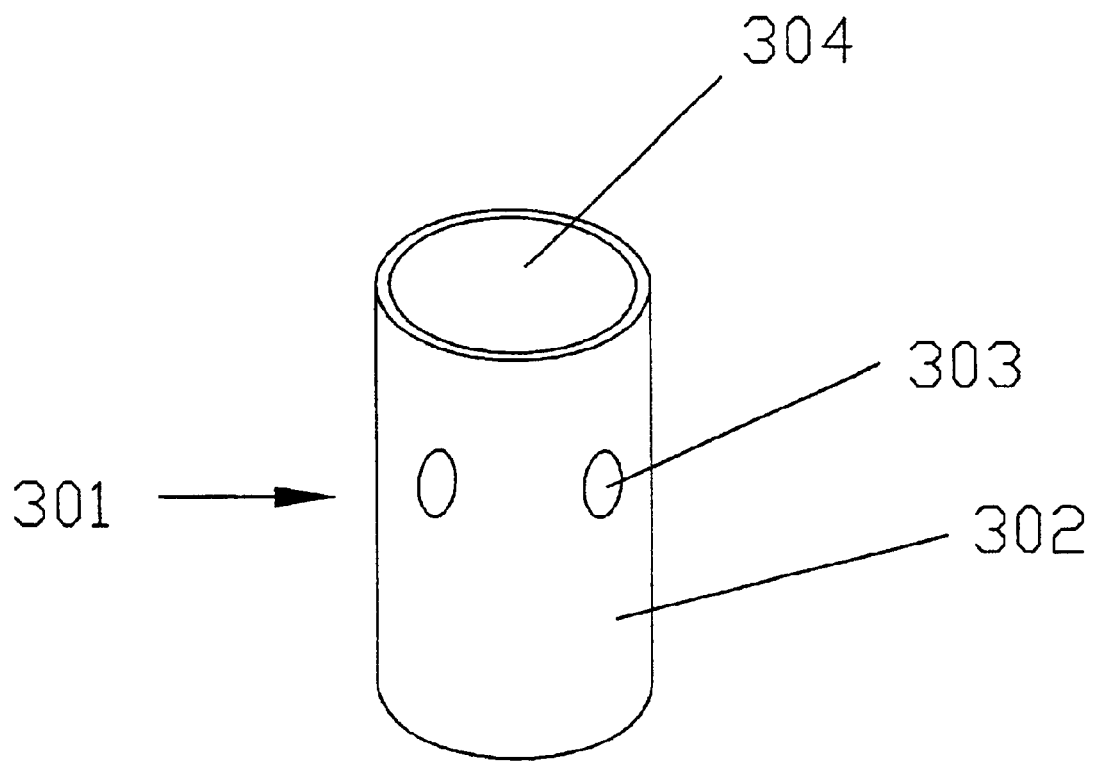
FIG. 3 is a perspective view of a cylindrical air tube component utilized in conjunction with the inflatable chuck insert of FIG. 2.

FIG. 3 illustrates the cylindrical sleeve 301 including a plurality of holes 303 formed around its body. In the preferred embodiment four holes of approximately ¼" diameter, each located 90 degrees away from the prior hole are formed at the same vertical height. The holes 303 permit the passage of compressed air. The sleeve 301 is preferably made of stainless steel to avoid corrosion.

With further reference to FIG. 4, the mechanism for gripping and tightening a cap will now be described in greater detail. Compressed air is fed through bore 403 in spindle shaft 4. The compressed air then flows into cavity 405, into bores 404 and 406, and air chamber 402. The air flows through the holes 303 of sleeve 301 and inflates the elastic insert 201. Note that the elastic insert 201 is shown in its deflated position in FIG. 4. Upon inflation, the elastic insert 201 tightly grips the circular periphery of the cap 40 in cavity 416 of the cap driver assembly 401. After securing the cap 40, the cap driver assembly 401 turns to tightly screw the cap 40 onto the neck of container 11 to the predetermined torque programmed in the console 27.

Servomotor technology and a computer program are utilized to stop the servomotor 8 at a predetermined torque setting. Parameters for setting the proper torque are entered in operator console 27. The console is elevated by post 28 as seen in FIG. 1 for ease of use. Briefly, it will be noted that the servomotor 8 is able to detect the error in rotation that is caused by the resisting force exerted on the cap 40. As a rule the greater the error, the greater the torque applied. The operation of this servomotor 8 will be explained hereinafter in further detail.

Once the predetermined torque is attained, vacuum is applied through port 67 on plate 19 illustrated in FIG. 1. The vacuum is transmitted through spindle shaft orifice 403 and exerts negative pressure on the insert 201 and contracts it to its original condition. In this manner, the cap driver assembly 401 provides for a quick release of the associated cap 40 before the chuck moves back up to start a new cycle. At that point, the cap driver assembly 401 is raised and the container 11 is indexed away from the cap torquing station. At the same time, a newly capped container 11 arrives at the torquing station to start the next cycle.

Figure 5:
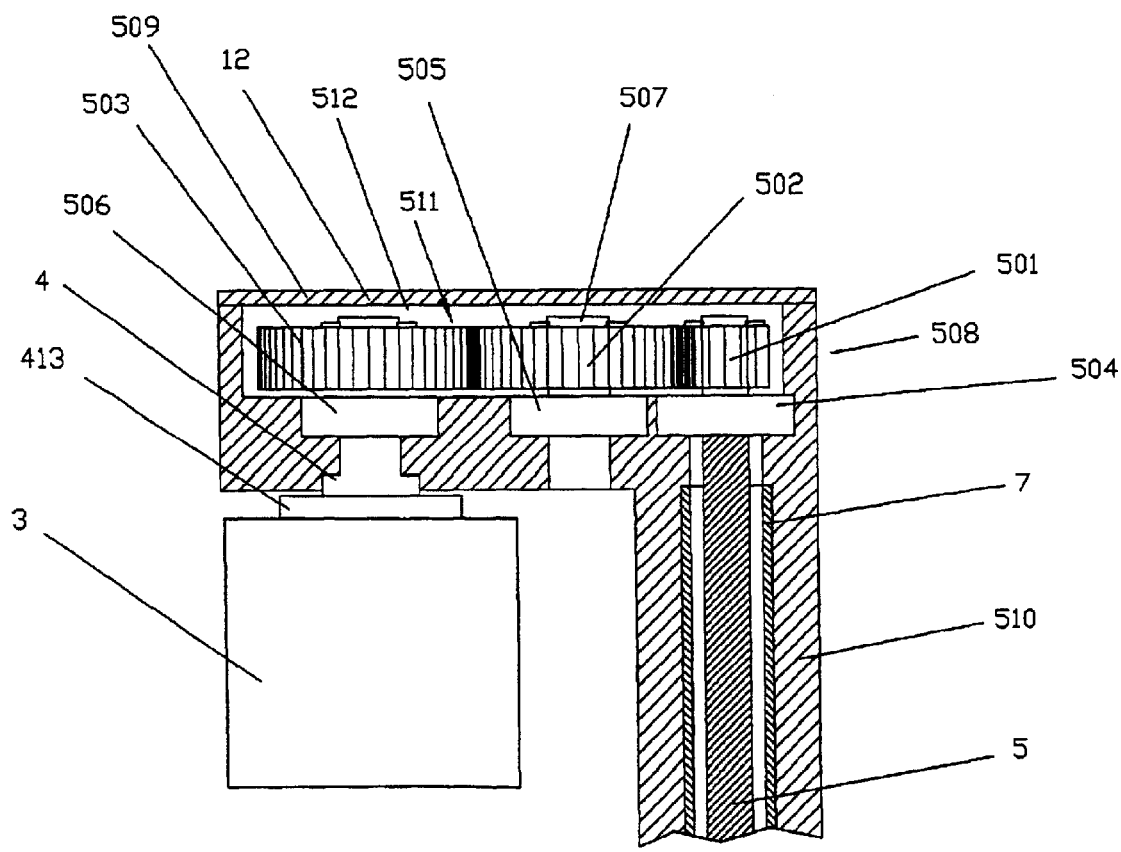
FIG. 5 is an orthogonal view of the gear mechanism within the capping head of the present invention.

FIG. 5 is an orthogonal view of the gear drive mechanism within the capping head 2 of FIG. 1. This mechanism serves to transmit a precisely controllable torque to each cap 40. Hollow shaft 5 is fixedly attached to the housing 508 of capping head 2 by means of suitable fasteners such as screws (not shown). The housing includes a top plate 509 and a housing body 510. The housing body has a central cavity 512 for accommodating a gear mechanism and two parallel side cavities for accommodating the two vertical shafts namely driver carrier shaft 5 and air/vacuum channel shaft 6 (shown in FIG. 1) which move up and down together to impart vertical movement to the capping head 12. Rotatable shaft 7, which is disposed inside driver carrier shaft 5 carries rotational motion in a clockwise direction as viewed from the top in FIG. 1 and FIG. 6. At its lowermost portion, rotatable shaft 7 is engaged with the motor shaft via spline mechanism 73 to be described hereinafter in further detail. External spur gear 501 is affixed to the end of rotatable shaft 7. At its uppermost portion, rotatable shaft 7 is engaged with spur gear 501. Rotatable shaft 7 moves up and down with driver carrier shaft 5.

When the input torque motor turns shaft 7 and the attached external spur gear 501 in a clockwise direction, this rotational movement is transmitted to counterclockwise movement of external spur gear 507, which in turn transmits clockwise rotation to external spur gear 503. Spur gear 503 transmits the rotational motion to spindle shaft 4, which in turn transmits it to the cap driver assembly 401. The capping head 12 is provided with antifriction bearings such as ball bearings 504, 505 and 506, which respectively support shafts 4, 7, and 507.

Figure 6:
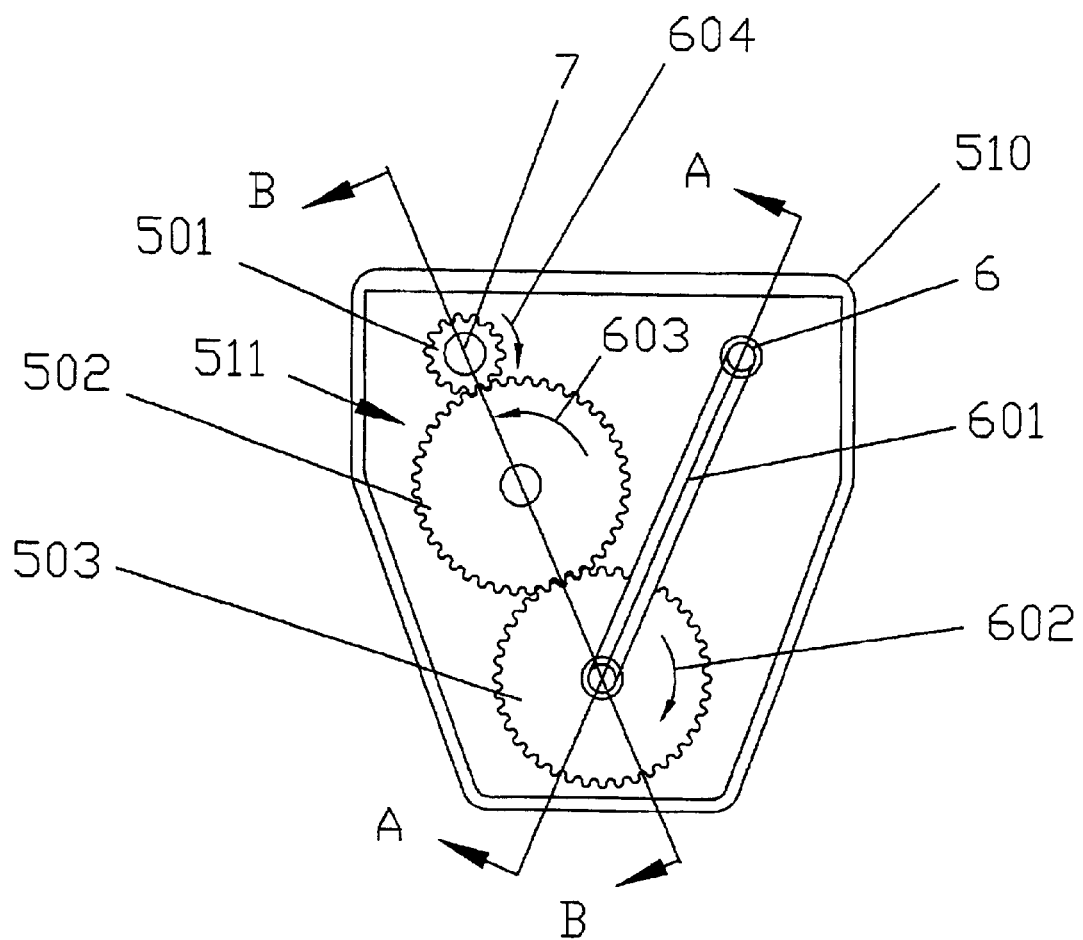
FIG. 6 is a plan view of the gear mechanism within the capping head of the present invention.

FIG. 6 is a top view of the capping head 12 with the top plate 509 removed showing the arrangement of the gear mechanism and shafts. Air/vacuum carrier shaft 6 is parallel to driver carrier shaft 5 and moves the cap driver assembly 401 up and down in conjunction with driver carrier shaft 5. Shaft 6 provides pressurized air and vacuum for the elastic gripper 201. The clockwise rotation of the spur gear 501 when shaft 7 turns is shown by the directional arrow 604. Spur gear 502 rotates in a counterclockwise direction as shown by directional arrow 603. Spur gear 503 rotates in a clockwise direction as shown by directional arrow 602. A channel 601 extends from shaft 6 to carry the air/vacuum from shaft 6 to channel 403 (refer to FIG. 4). The channel 601 is formed in the top plate 509 and cannot actually be seen when the top cover 509 is removed, but its location is shown in FIG. 6 for purposes of clarification.

Figure 7A:
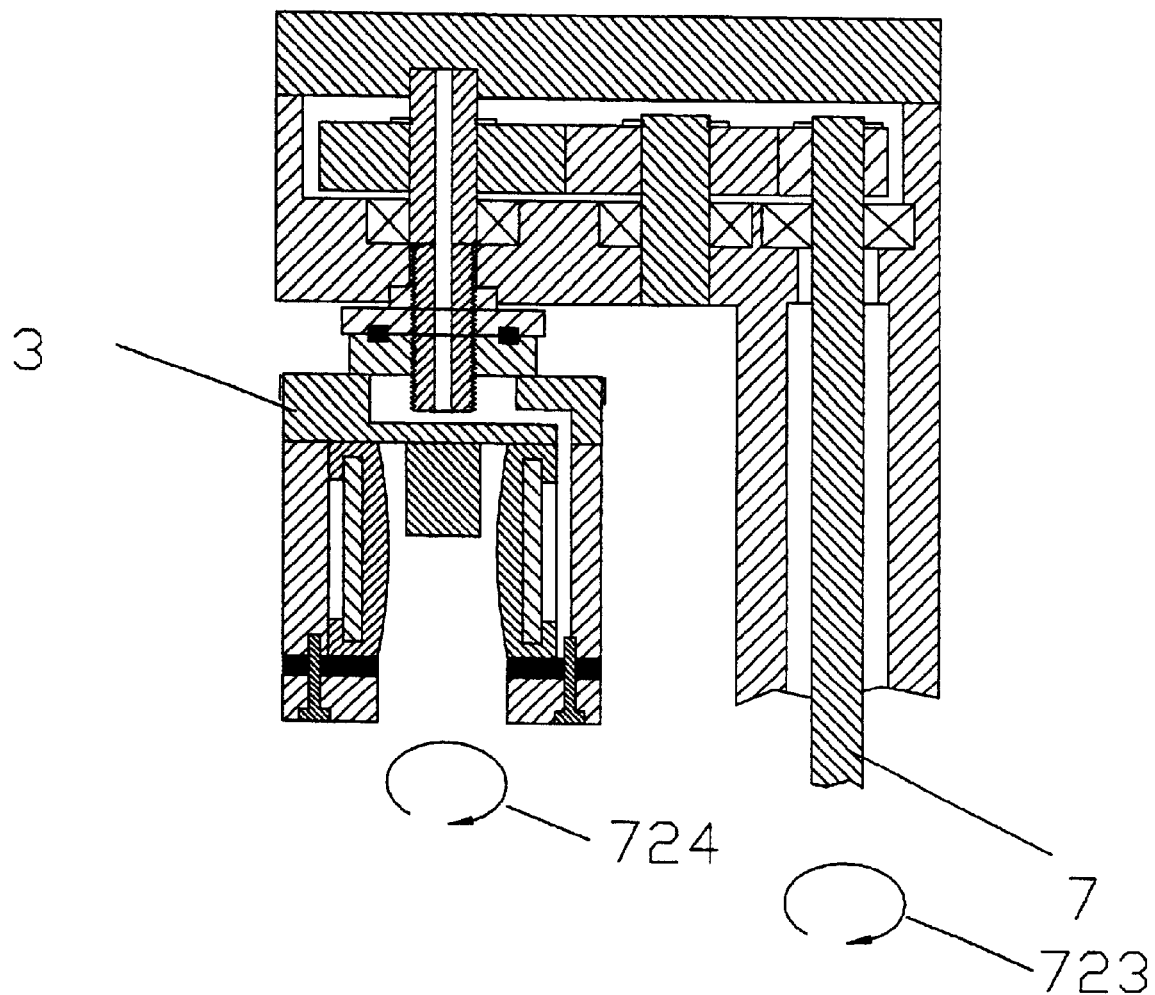
FIG. 7A is a cross-sectional view taken through the capping head along line A—A of FIG. 6.
Figure 7B:
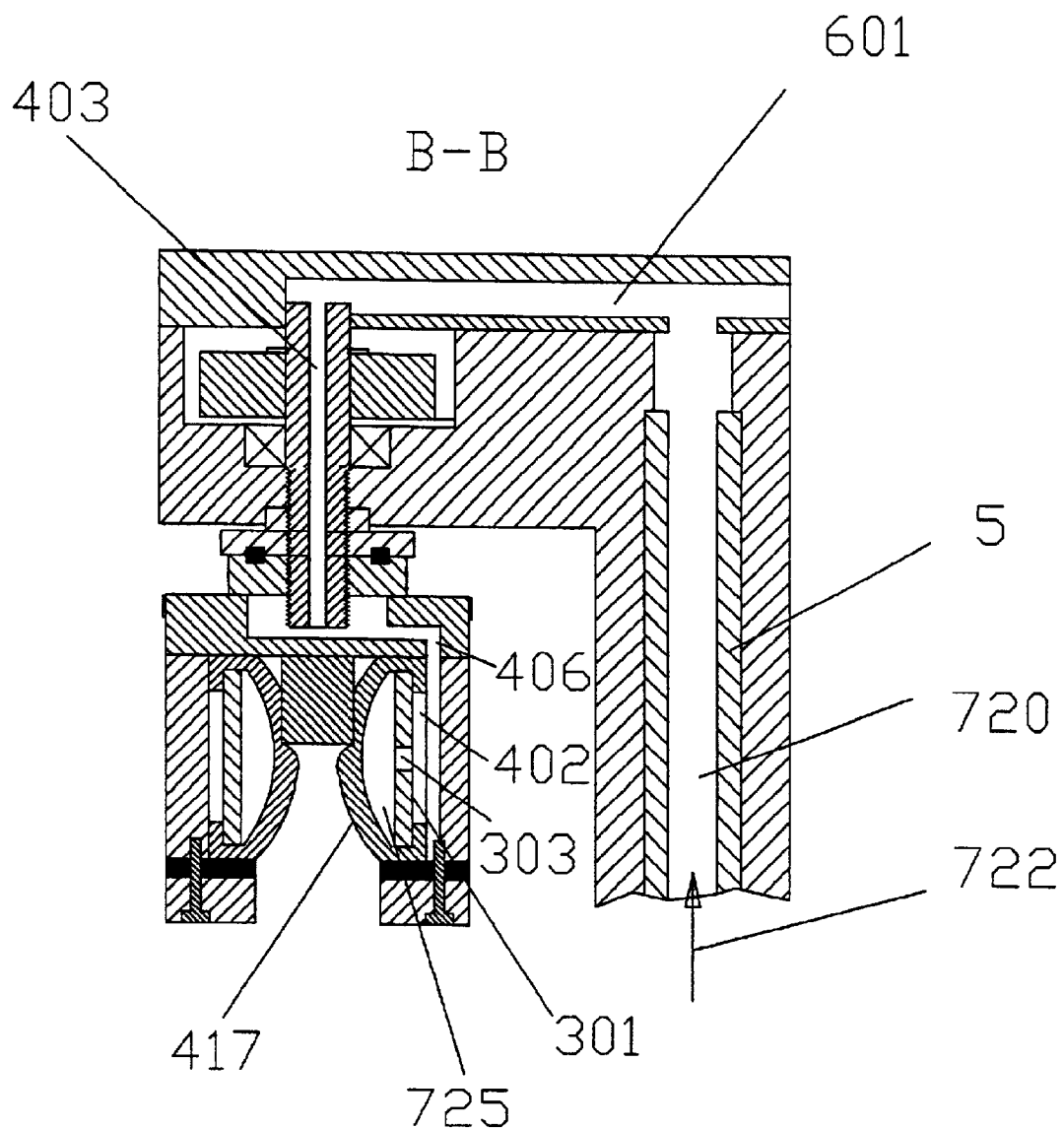
FIG. 7B is a cross-sectional view taken through the capping head along line B—B of FIG. 6 showing the inflatable chuck in a deflated condition.
Figure 7B:
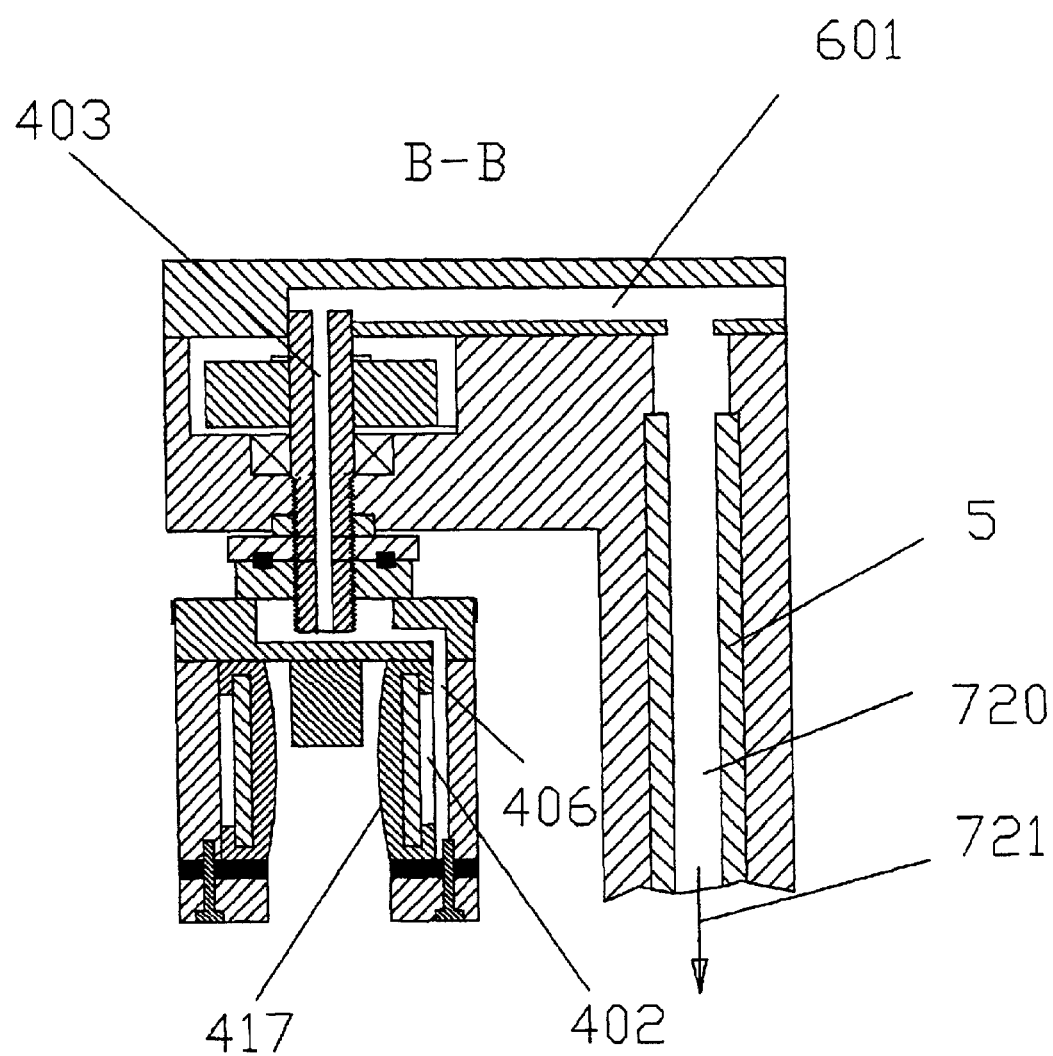

FIGS. 7A through 7B' are a series of cross-sectional views taken through the capping head 12 and the cap driver assembly 401 depicting the arrangement of the internal components thereof and their operation including the gear mechanism, shaft rotation and, compressed air/vacuum flow during actuation of the elastic gripper 201.

FIG. 7A is a sectional view taken along the line A—A of FIG. 6 showing capping head 12 and the cap driver assembly 401 and the components thereof, This illustration permits a full view of the rotatable drive shaft 7. The direction of rotation of rotatable drive shaft 7 and cap driver assembly 401 is shown by directional arrows 723 and 724 respectively.

FIG. 7B is a sectional view of the capping head 12 and the cap driver assembly along the line B—B of FIG. 6. The interior channel 720 of the hollow shaft 5 is illustrated. The channel 720 inside shaft 5 permits the compressed air to exhaust from the gripper 201 via air chamber 402, orifice 406, and cavity 405 either by opening a valve to exhaust the air or by applying vacuum to exhaust it more rapidly. Directional arrow 721 shows the direction of flow of the exhausted air or the applied vacuum. The gripper 201 is shown in a deflated condition in this view.

FIG. 7B' is a sectional view along the line B'—B' of FIG. 6. It is similar to FIG. 7B except that it illustrates the gripper 201 in an inflated condition. Compressed air enters the cavity 725 between the insert 201 and sleeve 301, which expands under the air pressure and actuates the gripper 201 to permit the gripping and torquing of caps 40. The path of the compressed air for actuation of the gripper 201 is indicated by directional arrow 722 which shows air flowing into channel 720 of the rotatable drive shaft 5 into channel 601, orifice 403, orifice 406, air chamber 402, holes 303 and into cavity 725 within the insert 201.

Figure 9:
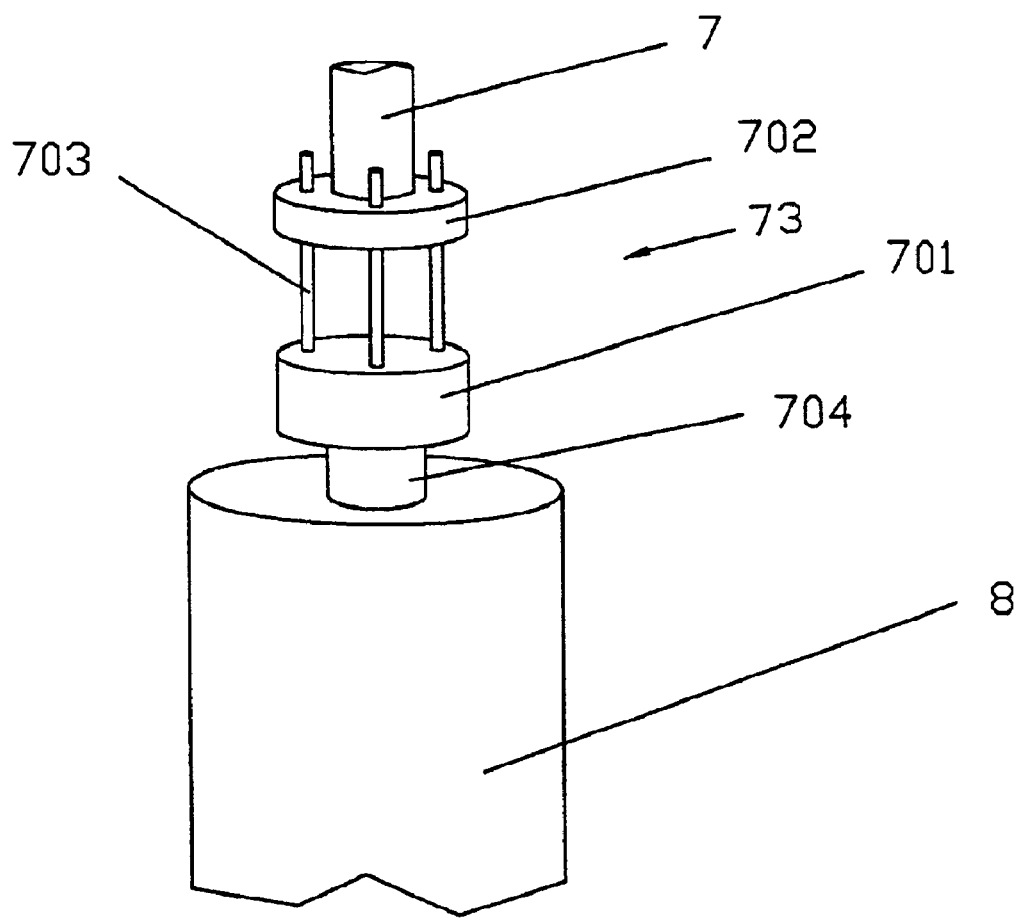
FIG. 9 is a perspective view of the spline mechanism of the present mechanism connecting the servomotor to a drive shaft.

Referring to FIG. 9 there is shown therein a spline mechanism, indicated generally at 73, which mechanically couples the servomotor 8 to the drive shaft 7. The spline mechanism 73 transfers rotations from the servomotor 8 to the rotatable shaft 7 in such a way that allows drive shaft 7 to move up and down simultaneously with rotation. As described hereinabove, downward movement of the capping head 12 is required for positioning the cap driver assembly 401 for gripping of caps to be torqued. After the torquing cycle is completed, the gripper 201 is released and the cap driver assembly 401 moves upwardly to allow the capped container to be removed and a new container to be brought into the torquing station. This up/down movement with simultaneous rotation of the drive shaft 7 is facilitated by the construction of the spline mechanism, indicated generally at 73, as seen in FIG. 9. Disk 701 is fixedly attached to the output shaft 704 of the servomotor 8. Disk 701 includes a plurality of finger shafts 703 permanently attached thereto. Disk 702 includes mating holes (shown in broken lines in FIG. 9) sized to a slip fit condition with each of the finger shafts 703 such that disk 702 is able to slide up and down in engagment with finger shafts 703. Disk 702 is fixedly attached to rotatable shaft 7, which carries the rotational motion when rotatable shaft 7 is moving up and down or when shaft 7 is stationary.

Figure 8A:
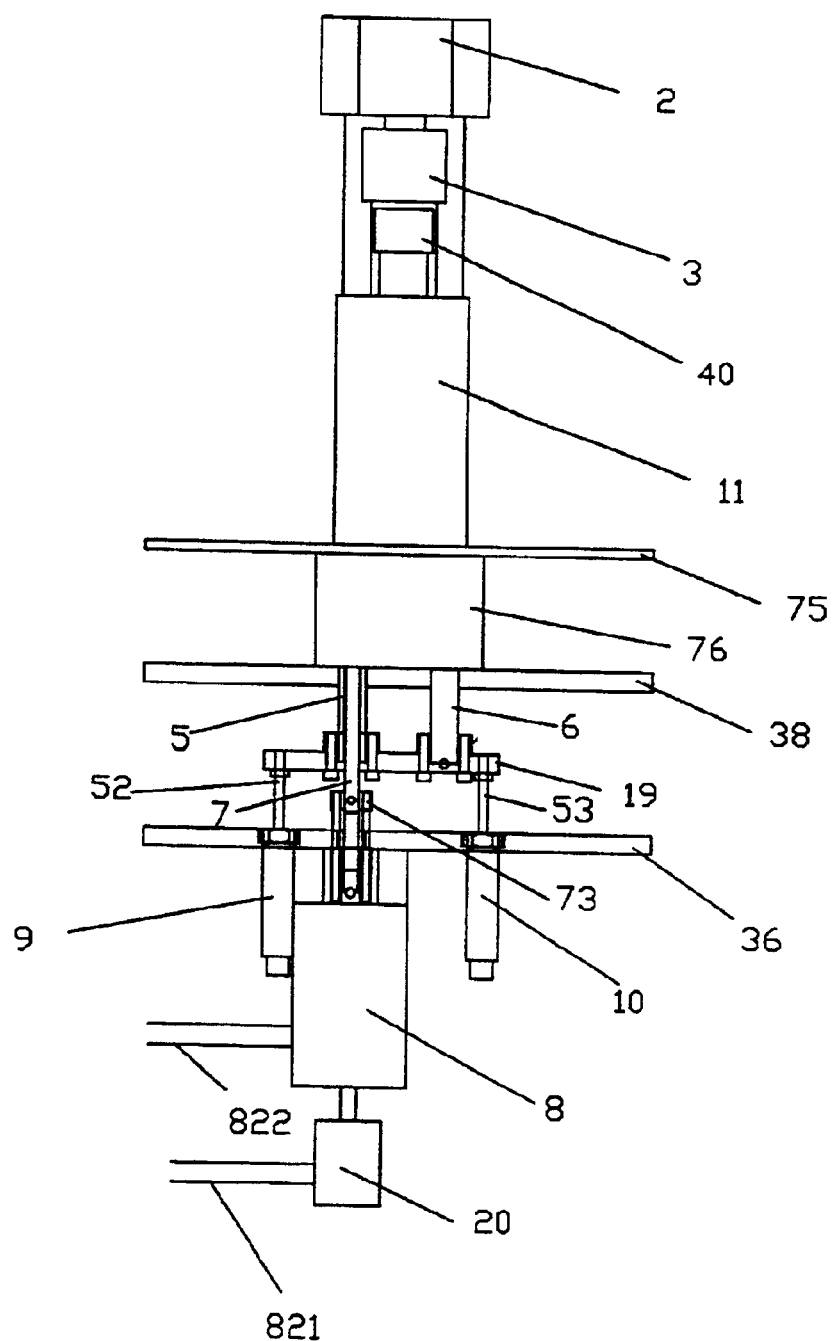
FIG. 8A is a side elevational view of the actuating mechanism for the present capping apparatus showing the capping head in the raised position.
Figure 8B:
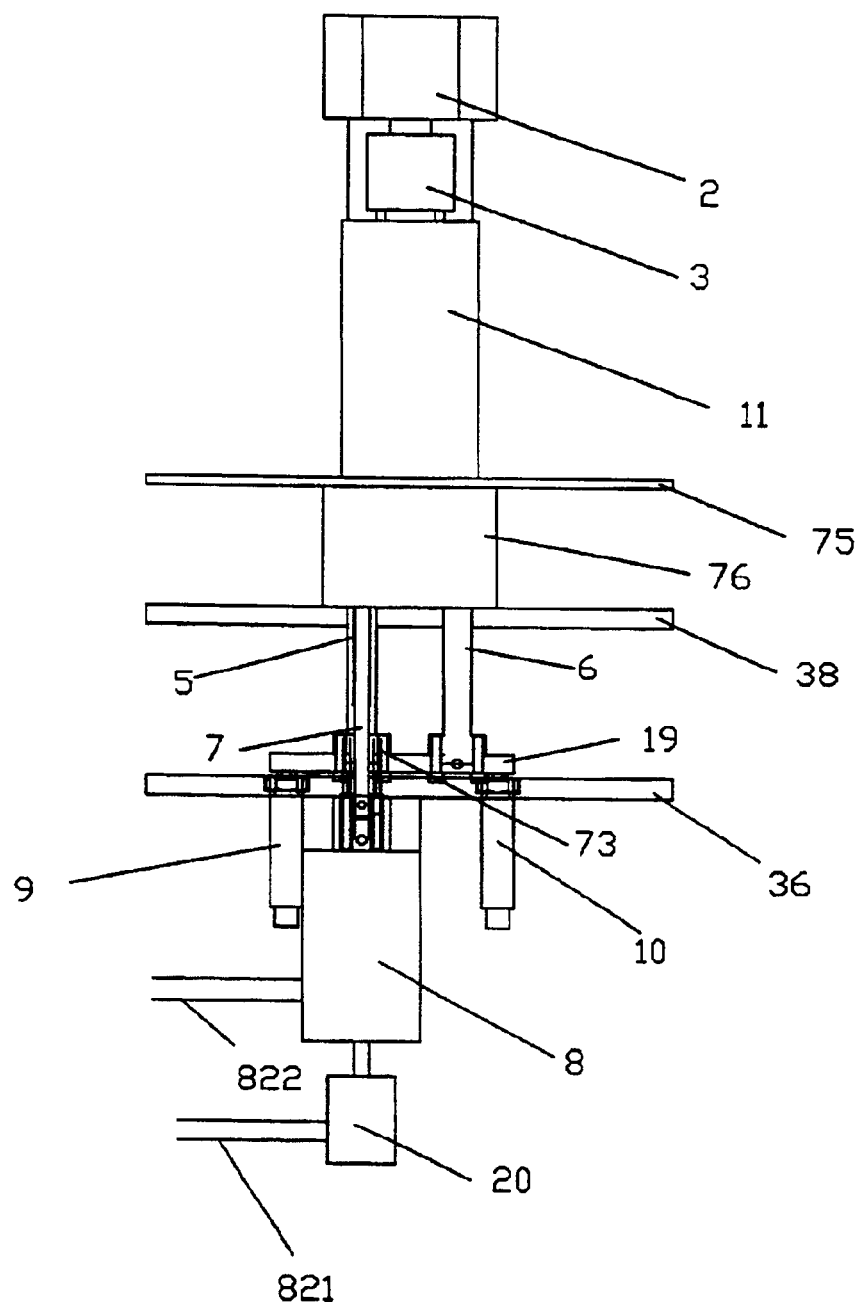
FIG. 8B is a side elevational view of the actuating mechanism for the present capping apparatus showing the capping head in the lowered position.
Figure 8C:
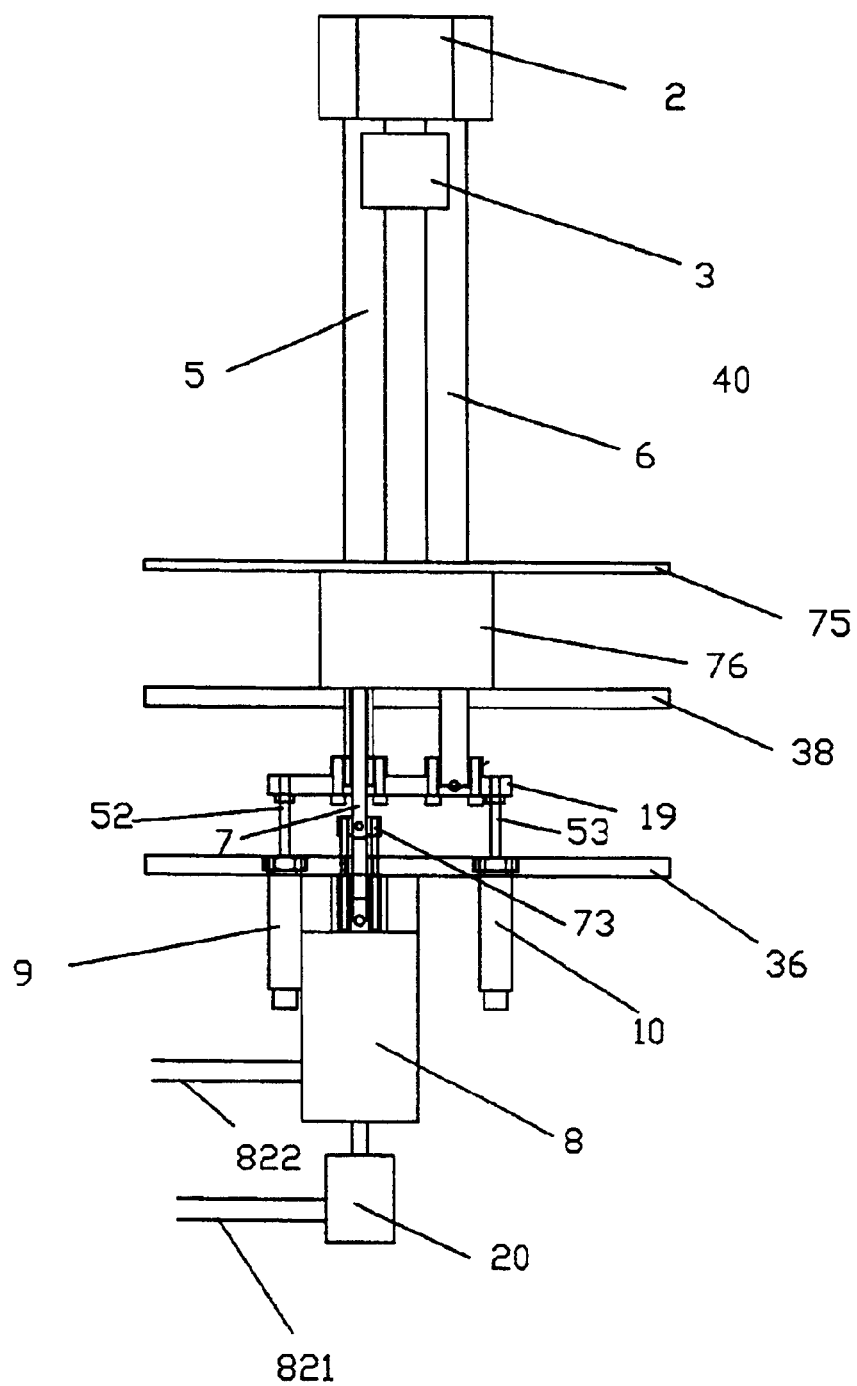
FIG. 8C is a side elevational view of the actuating mechanism for the present capping apparatus with the container and cap removed to show the vertical movement of the capping head by the drive carrier shaft and the air/vacuum channel shaft.

Referring to FIGS. 8A–8C there is shown an orthogonal view of the drive mechanism of the rotary capping apparatus 10 with the starwheel 16 removed for clarification purposes. FIG. 8A shows the capping head 12 in the raised position. When the capping head 12 is in such raised position, a container 11 can be delivered to a position underneath it for torquing by the cap driver assembly 401. Block 76 includes linear bearings (not shown) to guide the upward and downward movement of shafts 5 and 6 carrying the capping head 12 from a raised to a lowered position Cylinder rods 52 and 53 projecting from cylinders 98 and 99 are shown in an extended position in FIG. 8A. The servomotor 8 is provided with leads 822, which are electrically connected to the servoamplifier (not shown). The encoder 20 is also provided with leads 821, which are electrically connected to the servocontroller (not shown).

FIG. 8B is similar to FIG. 8A except that the capping head 12 is shown in its lowermost position. It will be noted that the cap 40 being applied to container 11 cannot be seen as it is inside cap driver assembly 401. When the capping head 12 moves to this lowermost position, the cylinder rods 52 and 53 are retracted within cylinders 9 and 10 and cannot be seen. At the position shown in FIG. 8B, the capping head 12 is ready to drive the cap 40 onto the neck of the container 11 and torque it to the preset value.

FIG. 8C illustrates the drive mechanism again in the raised position of FIG. 8A with the container 11 and cap 40 removed for purposes of clarity to show the vertical movement of the capping head 2 is supported by the drive carrier shaft 5 and the air/vacuum channel shaft 6, which move up and down together.

Figure 10:
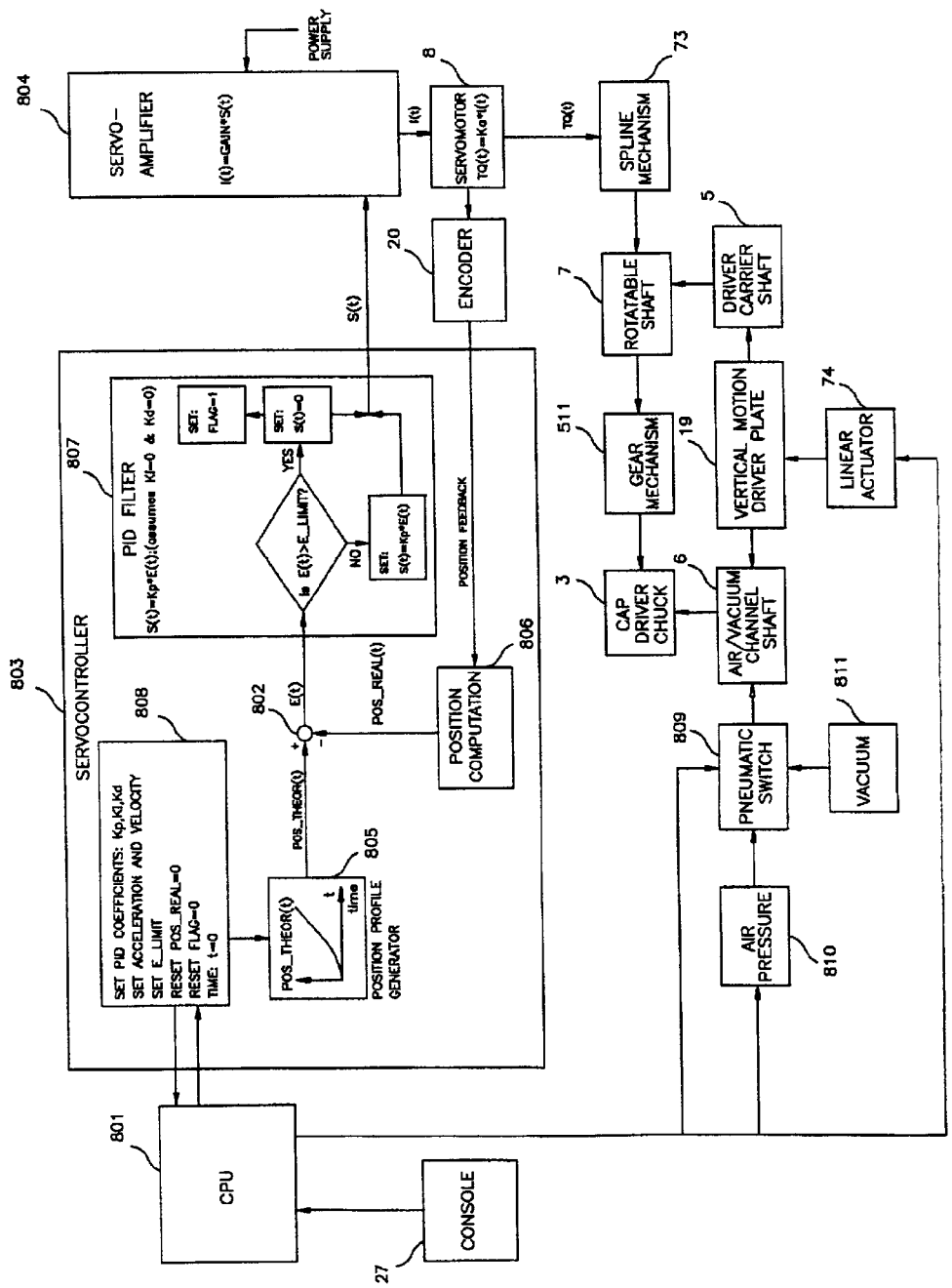
FIG. 10 is a schematic representation of the operation of the present rotary capping apparatus.

FIG. 10 is a schematic representation, which illustrates the operation of the rotary capping apparatus of the present invention. The operation of the present apparatus is controlled by a so-called closed loop control system. A closed loop system being one in which an actual measured variable (i.e. angular position) is sent back as feedback to the servocontroller 803 for comparison with the desired variable (i.e. angular position error) to provide control based on the error found in the comparison (i.e. desired position vs. actual position). The error between desired and actual position represents the torque applied to the cap when applying it to a container. When the desired torque has been applied, the control system stops applying torque, the container 11 is removed from the cap driver assembly 401, and a new container is moved into position.

Still referring to FIG. 10, the present control system includes an operator console 27, a central processing unit (CPU) 801, a servocontroller 803, a servoamplifier 804, a servomotor 8 and an encoder 20. The console 27 is connected to the CPU 801 for entry of parameters that control the movement and gripping action of the cap driver assembly 401. The servocontroller 803 is interfaced with CPU 801 for bi-directional communication.

The servocontroller 803 generates a theoretical position profile, which is a function of time, t: Pos-theor (t). The servocontroller 803 receives position feedback from an incremental position monitoring device such as encoder 20. The servocontroller 803 generates an output control signal S(t) which is sent to the servoamplifier 804. The output control signal is a function of time, t. The servocontroller 803 executes proportional, integral and derivative (PID) control as follows: The position feedback from the encoder 20 is sent to operating block 806 which generates the real position, POS_REAL(t) of the rotary capping apparatus as a function of time, t. The POS_REAL(t) is fed into a comparator junction 802.

In one embodiment of this invention, an incremental quadrature encoder is used with two channels: A and B, generating 500 pulses per revolution Channels A and B are shifted by +90 or −90 electrical degrees in relation to each other, depending on the direction of rotation. The servocontroller 803 can read incoming pulses from the encoder 20 and calculate precisely the current position of the drive shaft: POS_REAL(t). At the same time, junction 802 receives the theoretical position POS_THEOR(t) from operating block 805. At the beginning of each cap torquing cycle, POSITION PROFILE GENERATOR block 805 generates the POS_THEOR(t) from parameters received from the CPU 801. These parameters include the angular acceleration of the rotation of the capping apparatus, the angular velocity of the rotation of the present capping apparatus and an allowable position error, E LIMIT. These parameters can be changed via the console 27.

At junction 802 the theoretical position generated, POS_THEOR(t) is compared to the real position POS_REAL(t) and a Position Error, E(t) is generated. The mathematical relation is E(t)=POS_THEOR(t)−POS_REAL(t). This comparison is carried out by adding the theoretical position as a positive number and adding the real position as a negative number as indicated by the positive and negative symbols adjacent to junction block 802. The PID FILTER block 807 then generates the control signal S(t) as a function of the position error E(t). S(t) is the PID output and is obtained from the following well known mathematical expression for PID control: $S(t)=K_p*E(t)+K_i \int E(t)\,dt+K_d dE(t)/dt$. $K_p*E(t)$ is the proportional control term, $K_i \int E(t)\,dt$ is the integral control term and $+K_d dE(t)/dt$ $K_i$ is the derivative control term S(t) is the signal output. Kp, Ki and Kd are constant coefficients, which are experimentally determined and adjusted to produce an optimal control signal S(t), The adjustment of Ki and Kd results in greater stability of the motor.

For purposes of illustration, one embodiment setting $Ki=0$ and $Kd=0$ will provide an adequate control signal $S(t)$. Thus, $S(t)=Kp*E(t)$. The servocontroller 803 is programmed to set $S(t)$ to zero when the position error $E(t)$ exceeds a certain predetermined value E_LIMIT. The E_LIMIT value is adjustable from the console 27 and is stored in the CPU memory. If the error $E(t)$ is less than the predetermined value E_LIMIT, the control signal is set to $S(t)+Kp*E(t)$.

On the other hand if $E(t)$ is greater than E_LIMIT, then $S(t)$ is set to zero. At this point the FLAG is set to 1. Setting the FLAG to 1 causes the cycle to start anew. Thus, the maximum value of the signal $S(t)$ before it becomes zero is $Max(S)=Kp*E\_LIMIT$. The signal $S(t)$ is sent from the servocontroller 803 to the servoamplifier 804 where it is converted to a value of electrical current $I(t)$ by the following mathematical relationship: $I(t)=GAIN*S(t)$, where GAIN is a constant coefficient. The maximum current $I(t)$ is related to the maximum signal $S(t)$ as follows: Max $(I)=$ Gain*Max $(s)$; or Max $(I)=$Gain KpE_LIMIT. The servoamplifier 804 controls the servomotor 8 with the current $I(t)$. The servomotor 8 in turn converts the electrical current $I(t)$ into the torque $TQ(t)$ that is applied to the motor shaft. $TQ(t)=Ka*I(t)$, where Ka is a constant coefficient. The maximum torque is related to the maximum current as follows: Max $TQ=Ka*Max$ $(I)$; or Max $TQ=Ka*GAIn*Kp*E\_LIMIt$. Considering that Ka, Gain, Kp are constants, Ka*Gain*Kp is also a constant. Thus, Max TQ=CONSTANT E_limit. In summary, the servocontroller 803 reads the maximum torque after capping is completed and the cap driver assembly 401 cannot rotate any further due to the solid stop.

The position error (difference between Pos_THEOR(t) and POS_REAL(t) increases quickly since the theoretical motion profile, POS_THEOR(t) is calculated based on the continuous velocity, so POS THEOR(t) continues to increase. However, POS_REAL(t) is restricted and remains almost unchanged. As soon as the position error $E(t)$ exceeds the preset limit E_LIMIT, which results in reaching the torque associated with it according to MaxTQ= CONSTANT*E_LIMIT, the signal $S(t)$ will be reset to zero by the servocontroller 803 and consequently $I(t)=0$ as well as $TQ(t)=0$. When the servoamplifier 804 receives the incoming signal of $S(t)=0$, it will remove any voltage applied to the servomotor 8 resulting in no current being sent to the servomotor, i.e. $I(t)=0$. The servomotor 8 will release the torquing force from its shaft, and the servocontroller 803 will set a flag in block 808 noting this event for the CPU 801. As can be seen from MAXTQ=CONSTANT*E_LIMIT, the maximum applied torque is adjustable by setting the value of E_LIMIT. This value is entered and adjusted from the console 27.

Still referring to FIG. 10, the torque produced by the servomotor 8 is transmitted to the cap driver assembly 401 by way of spline mechanism 73, rotatable shaft 7, and the gear mechanism 511 as described in connection with FIGS. 1 and 9. At the same time that the hereinabove described servomechanism is controlling the torque of the cap driver assembly 401, the CPU 801 is operating the gripper 201 by inflating it prior to torquing and deflating it after torquing. Prior to any torquing action, the cap driver assembly 401 is moved to its lowest vertical position by the action of the vertical motion driver plate 19, which moves the cap driver assembly 401 up and down as previously described in conjunction with FIG. 1. An air pressure source 810 provides air to pneumatic switch 809, which sends air through the air/vacuum channel shaft 6 to the gripper 201 in the cap driver assembly 401. At the end of each cycle, the pneumatic switch 809 is activated and air pressure is cut off. Instead of air pressure, a vacuum source 811 provides vacuum through the pneumatic switch 809 and air/vacuum channel shaft 6 into the gripper 201. This permits rapid deflation of the gripper 201. After deflation, the cap driver assembly 401 is raised by the action of vertical motion driver plate 19, which is activated by linear actuator 74. Linear actuator 74 is activated by an electrovalve (not shown).

Figure 11:
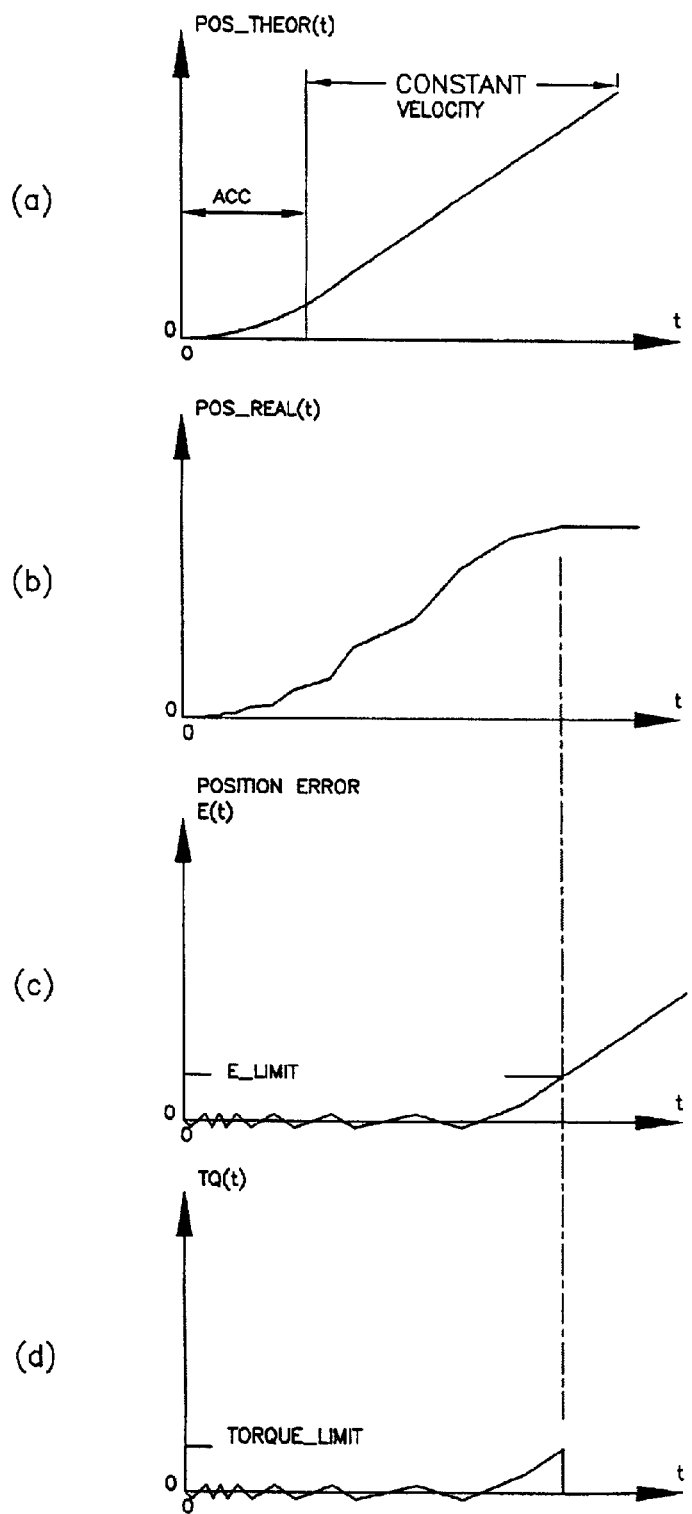
FIG. 11A is a graphical representation showing the theoretical position of the cap driver assembly generated by the servomotor as a function of time, (t)
FIG. 11B is a graphical representation of the actual position of the cap driver assembly generated by the servomotor as a function of time, (t)
FIG. 11C is a graphical representation showing the position error, which is the difference between the theoretical position and the actual position.
FIG. 11D is a graphical representation showing the torque as a function of time, (t)

FIG. 11 consists of four related diagrams. The first diagram, FIG. 11A shows the theoretical position of the cap driver assembly 401, POS_THEORET(t) that is generated by the servomotor 8 as a function of time, t. FIG. 11B shows the actual position of the cap driver assembly 401 as a function of time. FIG. 11C shows the position error, which is the difference between the theoretical position POS_THEOR(t) and the actual position POS_REAL(t). At the beginning of the cycle, the position error is small. As a cap 40 is driven onto a container 11, there is a point at which the position error begins to increase. This is the point at which the cap 40 has been completely screwed onto a container 11 and starts being torqued. At a further point in time, the position error reaches the value of E-Limit, at which point the cycle is stopped. FIG. 11D plots the torque as a function of time. The torque limit TORQUE_LIMIT is reached when E-LIMIT is reached.

Figure 12:
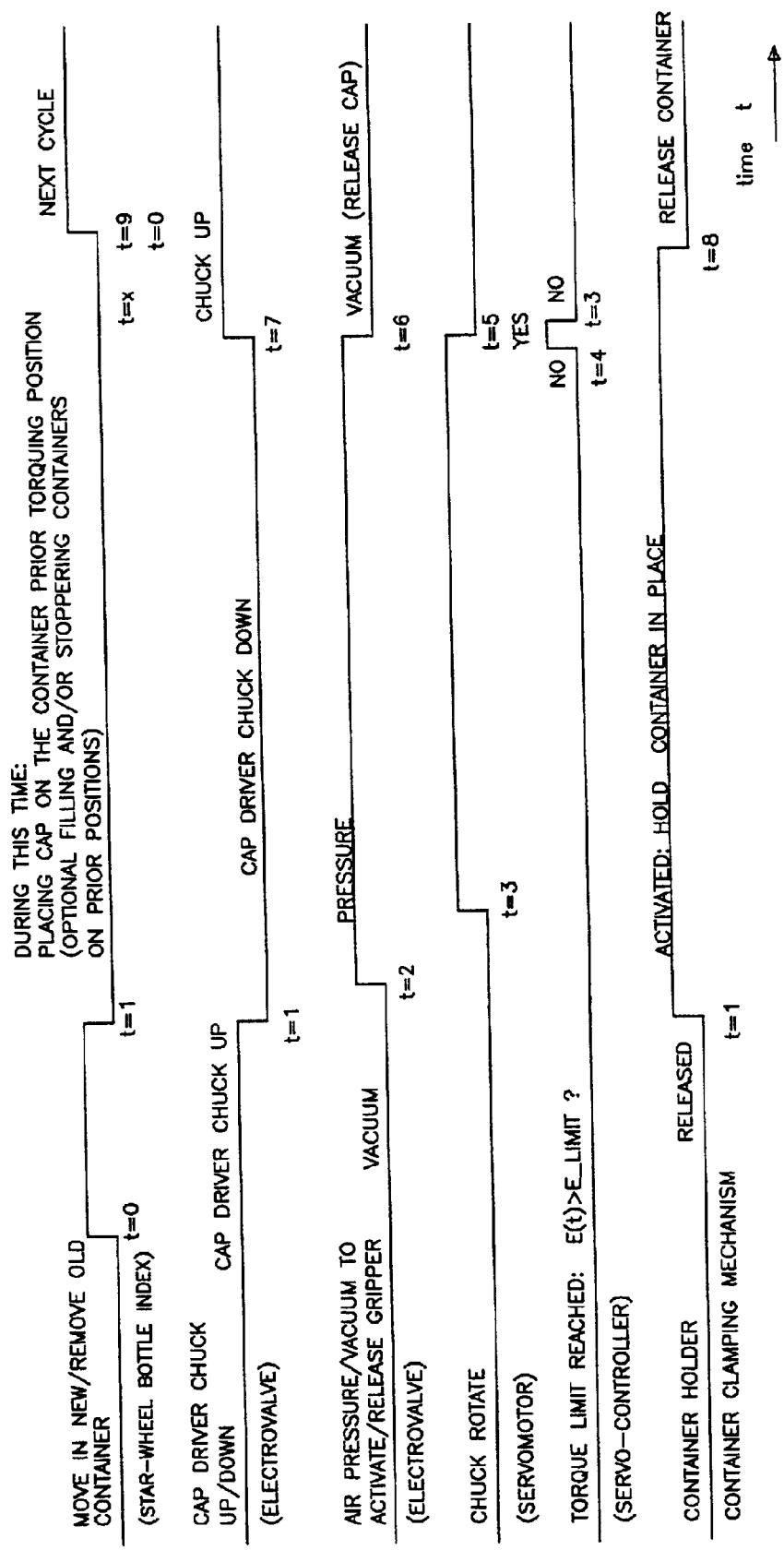
FIG. 12 is a diagrammatic representation showing the sequence of actions in the present capping process as a function of time, (t)

FIG. 12 depicts a timing sequence illustrating when specific actions in the present capping process occur. The horizontal lines in FIG. 12 represent time proceeding from left to right. In FIG. 12 if a portion of a horizontal line is raised it indicates that the subject device is active. The production cycle begins at $t=0$ time. Prior to the cap driving cycle, a new container 11 is moved in place by the star wheel 16. This happens between $t=0$ and $t=1$. During this time, the cap driver assembly 401 is in the up position, vacuum to the inflatable gripper 201 is applied, the cap driver assembly 401 is not being rotated, the torque limit has not been reached and the container clamping mechanism is released.

At time $t=1$ a container 11 has been moved into position, the cap driver assembly 401 is commanded by the CPU to move down, and the container 11 is held in place by the clamping mechanism. At time $t=2$ air pressure is applied to the gripper 201 so that a cap 40 is held in position. Thereafter, at $t=3$, the servomotor 8 is commanded to apply torque and to rotate the cap driver assembly 401 to screw the cap onto the container. This is continued until $t=4$, at which time the torque limit is reached. The cap 40 initially introduces a small resistance to the servomotor 8. Thus, the torque and associated position error $E(t)$ of the servomotor shaft is relatively small until the cap is screwed on almost all the way at which time the resistance starts to increase. As soon as the value of $E(t)$ exceeds the limit (i.e. E-LIMIT) as discussed hereinabove, the current (i.e. $I(t)$) is removed from the servomotor 8 via setting $S(t)=0$, where $E(t)$ is a position error calculated as a difference between theoretical position and a real position of the motor shaft. $S(t)$ is the outcome of the PID filter filtering $E(t)$, $I(t)$ is proportional to the $S(t)$ signal and motor torque $TQ(t)$ is proportional to $I(t)$. $S(t)$ is proportional to $E(t)$, thus $TQ(t)$ is proportional to $E(t)$. Since Max $E(t)=E\_LIMIT$, Max $TQ(t)$ is proportional to E_LIMIT. The event of $E(t)$ exceeding E LIMIT is marked as $t=4$ and the motor 8 will stop a moment later as a result of mechanical inertia of the load attached to its shaft and the fact that the current $I(t)$ was set to zero via $S(t)=0$. Immediately after that, at time $t=6$, the gripper 201 is commanded to release by application of vacuum. After the cap is released, at time $t=7$, the cap driver assembly 401 is commanded to move up to clear the container movement. At time t=8, the cap driver assembly 401 is in its up position and the container clamping mechanism is commanded to release the container. A moment later, at time t=9, the machine is ready to repeat the cycle.

Thus, again at time t=1, a cap is placed on the container at the prior position in preparation for torquing in the next cycle. At this juncture optional functions like filling the container with a liquid or powder may take place. These functions last until time t=x. The time t=8 will occur after t=7 or t=x, whichever is larger.

Figure 13:
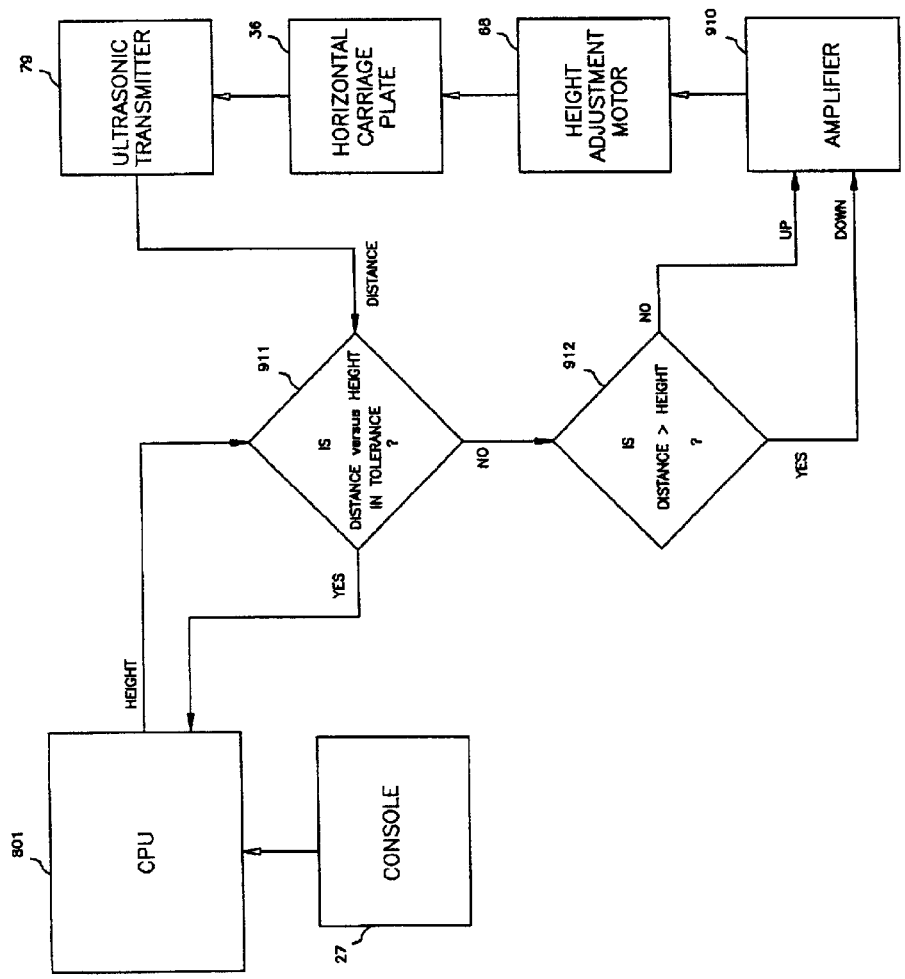
FIG. 13 is a schematic representation depicting the vertical height adjustment function of the present rotary capping apparatus.

FIG. 13 is a schematic representation depicting the operation of the feeder bowl automatic height adjustment function of the present rotary capping apparatus. This feeder bowl automatic height adjustment of the present invention is also controlled by a closed loop control system.

Referring to FIGS. 13 and 14 collectively, the present height adjustment system includes the operator console 27, the central processing unit (CPU) 801, the servocontroller 803 as described hereinabove and, in addition, an ultrasonic transmitter 76, the horizontal carriage plate 36, the height adjustment motor 68, an amplifier 910 and operating blocks 911 and 912.

In the height adjustment system the console 27 is connected to the CPU 801 for entry of parameters that control the height of the capping head 2. A signal from the ultrasonic transmitter representing the distance 85 shown in FIG. 14 to the horizontal carriage plate 36 is sent to the CPU 801 for positional feedback of the horizontal carriage plate 36. When the height adjustment motor 68 rotates, the horizontal carriage plate 36 moves up or down, and the capping head 12 moves with it. The distance between the carriage plate 36 and the bottom plate as at 85 corresponds to the height of container 11. The container height parameter is entered from the console 27 and stored for a particular product. When a new product is selected with a new value of height or when the height is manually changed from the console 27, the CPU 801 compares the height value with the measured distance as at 85 from the ultrasonic transmitter in operating block 911 shown in FIG. 13. If the distance 85 is greater than the height of the container 11, then the CPU 801 sends a signal to the amplifier 910 which is in turn sent to the height adjustment motor 68 rotating the lead screw 70 in a clockwise direction moving the horizontal carriage plate 36 and thus the capping head 12 downward. On the other hand, if the distance 85 is less than the height parameter in the console 27, then lead screw 70 is rotated in a counterclockwise direction moving the horizontal carriage plate 36 upward. Thus, depending on the difference in these two values, the CPU 801 sends a signal to drive the horizontal carriage plate 36 up or down until said difference is small with an allowable tolerance. Thus, the present apparatus will automatically adjust the height of the feeder bowl 22 to the correct level for the container being processed.

FIG. 14 is an orthogonal view of the present rotary capping apparatus 10 depicting the vibratory bowl 22 and the vibratory bowl support frame, indicated generally at 934, with the sheet metal cover 97 as seen in FIG. 1 removed to permit viewing of the internal components of the vibratory table adjustment mechanism. The vibratory bowl 22 is mounted on the free standing frame 934 such that vibrations are not transmitted to the rotary capping apparatus 10.

Frame 934 includes four vertical members of which only two, namely 931 and 932 are shown in FIG. 14. The lowermost portion of each vertical member is disposed within a thrust bearing. Only thrust bearings 928 and 929 associated with members 931 and 932 can be seen in this view. Such thrust bearings carry the weight of the frame 934 and bowl 22. Frame 934 is also provided with a top horizontal plate 930 and a bottom horizontal plate 933. The frame 934 can be moved up or down via rotations of motor 921. A leadscrew is attached to each of the vertical frame members; however, only leadscrews 855 and 856 associated with members 931 and 932 can be seen in FIG. 14.

A drive pulley 925 is attached to the shaft of motor 921 to drive the upward/downward movement of the frame 934 via belt 926. Although each leg of the vibratory frame is provided with such a pulley, only pulleys 923 and 924 can be seen in this view. It will be understood that belt 926 surrounds and engages all four pulleys. Rotation of the pulleys in one direction causes the frame 934 to move upwardly and rotation in the opposite direction causes the frame 934 to move downwardly.

A sensor 87 is mounted on the rotary capping apparatus 10 to detect the lower edge 920 of the vibratory bowl 22. More particularly, sensor 87 is mounted on bracket 86, which is in turn mounted on track support plate 80. The track support 80 also carries the feeder track 97. The track support 80 is supported by a set of shafts 81 that are attached to carriage plate 36. A feeder track 97 for the disbursement of caps 40 is fixedly attached to the vibratory bowl 22. Container caps 40 exit the vibratory bowl 22 through feeder track 97 and are delivered into the transfer track 23.

Still referring to FIG. 14, the height adjustment is calculated based on an offset such that the feeder track 87 and the transfer track 23 are at the same level and the container caps 40 can move freely. During installation of the machine, this is accomplished by moving the sensor 87 on bracket 86 such that it detects the edge 920 of the vibratory bowl when the feeder track 97 and transfer track 23 are on the same level. Thereafter, the height adjustment of the tracks 97 and 23 is automatic.

When an operator enters a new container height in the CPU 801 via the console, the height of transfer track 23 is determined by the procedure described hereinabove in connection with FIG. 13. As the sensor 87 is moved on transfer track 23 to accommodate the new height setting, the sensor moves away from edge 920 of the vibratory bowl 22. The CPU 801 then commands motor 921 to rotate and move the vibratory bowl frame 934 up or down to align the edge of the bowl 22 with the sensor 87, which event is detected by the sensor and a signal is sent to the CPU 801. A rotating wheel (not illustrated) or other alternative transfer means is functionally disposed above the caps 40 within transfer track 23 so as to advance the caps 40 into position at the cap placement station 44.

Figure 15:
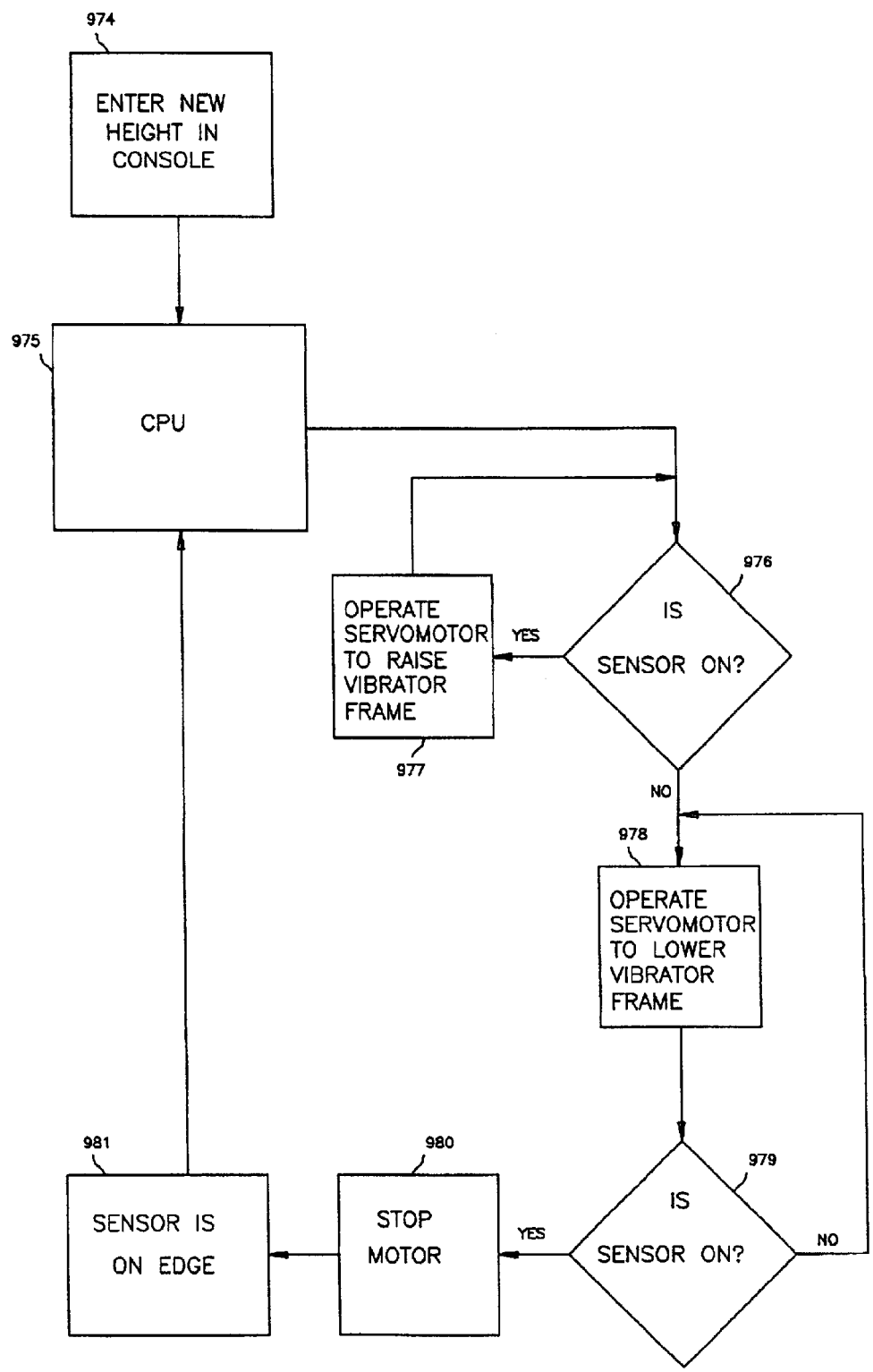
FIG. 15 is a schematic representation depicting the vertical height adjustment function of the secondary supporting frame.

FIG. 15 is a schematic diagram depicting the operational steps followed by the present capping apparatus in order to move the vibratory bowl frame 934 to a new height setting. As described hereinabove, an operator first enters a desired new height in the console. This is represented by step 974 in FIG. 15. In the next step 975, the new height is sent to the CPU. The CPU then sends the new height parameter to operating block 976 which determines whether the sensor 87 is on. If the sensor 87 is on, then a signal is sent to the motor 921 for raising the vibratory frame as at block 977 in FIG. 15. If the sensor 87 is not on, then a signal is sent to the motor 921 to lower the vibratory bowl frame 934. After the motor 921 is operated to lower the frame 934, the sensor is checked again as at block 979. If the sensor 87 is still not on, this process continues and the operator continues to lower the vibratory frame. Once the sensor 87 is on, the motor is stopped as at block 980. When the present apparatus recognizes that the sensor 87 is on the edge 920 of bowl 22 as at box 981, a completion signal is transmitted to the CPU.

It will be apparent from the foregoing description that this invention provides for a variety of improved features with respect to rotary capping apparatus and to closure grasping and torquing apparatus. The level of torque employed in securing caps on containers is digitally and precisely adjustable and can be conveniently reset by entering the appropriate parameters on a computer console.

Although not specifically illustrated in the drawings, it should be understood that additional equipment and structural components will be provided as necessary, and that all of the components described hereinabove are arranged and supported in an appropriate fashion to form a complete and operative system incorporating features of the present invention.

Moreover, although illustrative embodiments of the invention have been described, a latitude of modification, change, and substitution is intended in the foregoing disclosure, and in certain instances some features of the invention will be employed without a corresponding use of other features. Accordingly, it is appropriate that the appended claims be construed broadly and in a manner consistent with the scope of invention.

What is claimed is:

1. A rotary capping apparatus for applying screw-on type caps to containers, said apparatus comprising:
    a primary supporting frame having a plurality of vertical leg members;
    a cap driver assembly including an inflatable gripping means for application of a predetermined torque to the screw-on type caps, said cap driver assembly being mechanically coupled to said capping head;
    primary height adjusting means for imparting vertical movement to said capping head;
    a driving means including a servomotor for transmitting a predetermined torque to said cap driver assembly, said driving means being mounted on said height adjusting means and mechanically coupled to said capping head;
    container indexing means mechanically attached to said driving means for synchronous advancement of said containers to said cap driver assembly for torquing;
    a capping head disposed in vertically adjustable relation to said primary supporting frame, wherein said capping head includes a housing containing a gear mechanism and at least one input shall having a hollow core for transmission of torque from said driving means to said cap driver assembly, said core being disposed in fluid communication with an inflatable gripping means permitting the flow of compressed air and vacuum thereto, wherein said at least one input shaft is mechanically connected to said driving means by an axially extensible spine mechanism that permits simultaneous rotation and vertical extension of said at least one shaft during operation of said driving means; and
    closed loop controlling means for applying said predetermined torque further including:
    (a) a central processing unit for conducting proportional, integral, and derivative control calculations,
    (b) an operator console for setting parameters that govern application of said torque transmitted by said cap driver assembly to said caps, and
    (a) a servocontroller interfaced for bidirectional communication with said central processing unit, said servocontroller generating an output signal to said servomotor based on the position of said cap driver assembly for torquing said caps such that said predetermined torque is attained.

2. The rotary capping apparatus of claim 1 wherein said inflatable gripping means includes a elastic gripper disposed about a cylindrical sleeve forming an expandable air chamber therebetween, said chamber being disposed in fluid communication with a source of compressed air such that said gripper is inflatable to engage said caps for application of said torque.

3. The rotary capping apparatus of claim 2 wherein said expandable air chamber is simultaneously in fluid communication with a vacuum source for evacuation of said air chamber.

4. The rotary capping apparatus of claim 1 including a secondary supporting frame having adjustable leg members and being disposed adjacent to said primary supporting frame, said secondary supporting frame being isolated from said primary supporting frame to prevent transfer of vibration therebetween.

5. The rotary capping apparatus of claim 4 wherein said secondary supporting frame includes a cap dispensing means mounted thereon.

6. The rotary capping apparatus of claim 5 wherein said cap dispensing means is a vibratory cap feeding bowl.

7. The rotary capping apparatus of claim 5 wherein said cap dispensing means further includes a cap placement station.

8. The rotary capping apparatus of claim 5 wherein said secondary supporting frame includes automatic secondary height adjusting means.

9. The rotary capping apparatus of claim 8 wherein said automatic secondary height adjusting means further includes:
    (a) a sensing means mounted on said primary height adjusting means in functional alignment with said cap dispensing means,
    (b) a servomotor including amplifying means mounted on said secondary supporting frame,
    (c) a belt and pulley mechanism driven by said servomotor and engaging said adjustable leg members for raising and lowering said secondary supporting frame, and
    (d) a central processing unit for controlling said amplifying means to automatically raise and lower said secondary supporting frame to a predetermined height to process a selected product.

10. The rotary capping apparatus of claim 9 wherein said sensing means includes an ultrasonic transmitter.

11. The rotary capping apparatus of claim 1 wherein said container indexing means further comprises a rotatable starwheel having a plurality of radially disposed slots formed therein for incrementally advancing said containers to said cap driver assembly for torquing.

12. The rotary capping apparatus of claim 11 wherein said container indexing means further includes a conveying means for delivery of said containers to said rotatable starwheel.

13. An improved rotary capping apparatus for applying screw-on caps to containers, said apparatus including a supporting frame, a cap drive for application of torque to said caps, driving means for transmitting a predetermined torque to said cap driver, and container indexing means for delivery of said containers to said cap driver, said improvements comprising:

a capping head disposed in vertically adjustable relation to said primary supporting frame, wherein said capping head includes a housing containing a gear mechanism and at least one input shaft having a hollow core for transmission of torque from said driving means to said cap driver assembly, said core being disposed in fluid communication with an inflatable gripping means permitting the flow of compressed air and vacuum thereto, wherein said at least one input shaft is mechanically connected to said driving means by axially extensible spline mechanism that permits simultaneous rotation and vertical extension of said at least one shaft during operation of said driving means; and closed loop controlling means for calculation of said predetermined torque further including:
(a) a central processing unit for setting parameters that govern application of said torque transmitted by said cap driver, and
(b) a servocontroller interfaced for bidirectional communication with said central processing unit, said servocontroller generating an output signal to said driving means based on the position of said cap driver for torquing said caps such that said predetermined torque is attained.

* * * * *